(12) United States Patent
Luukas et al.

(10) Patent No.: US 7,988,741 B2
(45) Date of Patent: Aug. 2, 2011

(54) SPECIFIC NAPHTHALMIDE-TYPE DYES, DYE COMPOSITION COMPRISING AT LEAST ONE SUCH DYE, PROCESS USING SAME AND USES

(75) Inventors: Tiina Luukas, Sevran (FR); Andrew Greaves, Magny le Hongre (FR); Hervé David, La Varenne Saint Hilaire (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/904,526

(22) Filed: Oct. 14, 2010

(65) Prior Publication Data

US 2011/0113572 A1 May 19, 2011

Related U.S. Application Data

(63) Continuation of application No. 11/795,870, filed as application No. PCT/FR2007/050995 on Mar. 23, 2007, now abandoned.

(60) Provisional application No. 60/792,957, filed on Apr. 19, 2006.

(30) Foreign Application Priority Data

Mar. 24, 2006  (FR) ..................................... 06 02608

(51) Int. Cl.
*A61Q 5/10* (2006.01)
*C07D 221/14* (2006.01)

(52) U.S. Cl. ............ 8/405; 8/407; 8/431; 8/435; 546/98

(58) Field of Classification Search .............. 8/405, 407, 8/431, 435; 546/98
See application file for complete search history.

(56) References Cited

U.S. PATENT DOCUMENTS

| | | | |
|---|---|---|---|
| 3,625,947 A | 12/1971 | Nogochi et al. | |
| 4,508,900 A | 4/1985 | Schonberger et al. | |
| 4,595,756 A | 6/1986 | Schonberger et al. | |
| 5,235,045 A * | 8/1993 | Lewis et al. | 546/99 |

FOREIGN PATENT DOCUMENTS

| | | |
|---|---|---|
| CH | 520 677 | 3/1972 |
| DE | A-23 59 399 | 6/1975 |
| DE | A-38 43 892 | 6/1990 |
| DE | A-41 33 957 | 4/1993 |
| DE | A-195 43 988 | 5/1997 |
| EP | A-714 954 B1 | 6/1996 |
| EP | A-0 770 375 | 5/1997 |
| FR | 1557945 | 2/1969 |
| FR | A 2 010 444 | 2/1970 |
| FR | A 2 162 181 | 7/1973 |
| FR | A-2 733 749 | 11/1996 |
| FR | 2 801 308 | 5/2001 |
| GB | 1026978 | 4/1966 |
| GB | 1153196 | 5/1969 |
| JP | 88-169571 | 1/1990 |
| JP | 2004095492 | 3/2004 |
| WO | WO 93/18789 A | 9/1993 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 2005/074872 A1 | 8/2005 |
| WO | WO 2005/075574 A1 | 8/2005 |

OTHER PUBLICATIONS

STIC Search Report dated Mar. 11, 2011.*
Langlois et al., "N-chloromethyl quinuclidinium derivatives: A new class of irreversible ligands for 5-HT3 receptors," Bioorganic and medicinal chemistry letters, vol. 4, No. 7, 1994, pp. 945-948.
Database registry, American Chemical Society (ACS); file registry, RN=81494-75-9, Nov. 16, 1984, Pyridinium, 1-[2-[6-(dimethylamino)-1,3-dioxo-1H-benz[de]isoquinolin-2(3H)-yl]ethyl]-(9CI) (CA Index name).
Derwent Abstract for JP 2004-095492, published Mar. 25, 2004.
Tian et al., "Two-path photo-induced electron transfer in naphthalimide-based model compound," J. Chem. Soc., Perkin Trans. 2, vol. 3, 1999, pp. 545-549.
Preliminary Search Report for FR 0602608, dated Feb. 8, 2007.
Konstantinova et al., "The Synthesis, Properties and Application of Some 1, 8-napthaliminde Dyes," Dyes and Pigments, 45 (2000) 125-129.
Gunnlaugsson et al., "Dual Responsive Chemosensors for anions: The Combination of Fluorescent PET (Photoinduced Electron Transfer) and Colorimetric Chemosensors in a Single Molecule," Tetrahedron Letters, 44 (2003), 6575-6578.
Shepard et al., "Imidazolium and Imidazolinium Salts as Topical Antiseptics," J. Am. Chem. Soc. 1947, 69, 2269-2270.

* cited by examiner

*Primary Examiner* — Eisa B Elhilo
(74) *Attorney, Agent, or Firm* — Finnegan, Henderson, Farabow, Garrett & Dunner

(57) ABSTRACT

The present application relates to a novel family of cationic naphthalimide compounds that can be used as a direct dye, and to a dye composition for the dyeing of keratin fibers, in particular human keratin fibers such as the hair, comprising, in a suitable dyeing medium, at least one such compound. The present application also relates to the dyeing process using this composition and its uses.

35 Claims, No Drawings

SPECIFIC NAPHTHALMIDE-TYPE DYES, DYE COMPOSITION COMPRISING AT LEAST ONE SUCH DYE, PROCESS USING SAME AND USES

This is a continuation of application Ser. No. 11/795,870, filed Jul. 24, 2007 now abandoned, which is the National Stage of International Application No. PCT/FR2007/050995, filed Mar. 23, 2007, claiming priority to French Application No. 06-02608, filed Mar. 24, 2006, and claiming the benefit of U.S. provisional application No. 60/792,957, filed Apr. 19, 2006, the content of all of which are incorporated herein by reference.

The present application relates to naphthalimide-type dyes, to their use as direct dyes for dyeing keratin fibres and also to the dye compositions comprising such compounds.

It is known practice to dye keratin fibres by direct dyeing. The process conventionally used in direct dyeing consists in applying to the keratin fibres direct dyes, which are coloured and colouring molecules that have an affinity for the fibres, leaving the dyes on the fibres, and then rinsing the fibres.

It is known practice, for example, to use direct dyes of the nitrobenzene, anthraquinone or nitropyridine type, dyes of the azo, xanthene, acridine or azine type or triaryhnethane dyes, for example.

The colourations that result therefrom are particularly chromatic colourations, that are, however, temporary or semi-permanent. This is because the nature of the interactions which bind the direct dyes to the keratin fibre, and their desorption from the surface and/or the core of the fibre mean that the dyeing power and the resistance to washing or to perspiration of the dyes can still be considered to be insufficient. Some direct dyes can also be light-sensitive due to the poor resistance of the chromophore with respect to photochemical attacks, leading over time to fading of the colouration of the hair.

In order to obtain a more visible colouration, it is known practice to bleach the keratin fibres. This bleaching of the fibres is carried out by applying an oxidizing agent. However, direct dyes can be sensitive to the action of oxidizing agents, which generally makes them difficult to use under these conditions. Moreover, the use of an oxidizing agent can substantially degrade the cosmetic properties of the keratin fibres.

Moreover, naphthalimide-type derivatives have been known in the prior art since the 1960s, in particular as optical brighteners or whitening agents for synthetic textile products such as acrylic textile products or those made of cellulose acetate. Among the documents that illustrate this use, mention may be made of U.S. Pat. No. 3,625,947, U.S. Pat. No. 4,508,900 and U.S. Pat. No. 4,595,756 and application FR-A-1 557 945, which relates to cationic 4-alkoxynaphthalimide compounds, patent application FR-A-2 010 444, which relates to cationic 4,5-dialkoxynaphthalimide compounds, and application FR-A-2 162 181, which relates to azo dyes comprising a naphthalimide group.

In the field of the direct dyeing of keratin fibres, there exists a real need to search for direct dyes that are very chromatic and resistant to outside agents such as inclement weather, washing and perspiration.

There also exists a real need to have dyes which make it possible to obtain chromatic colours and which are stable in an oxidizing medium. There also exists a real need to have direct dyes which make it possible to lighten keratin fibres, even dark keratin fibres, without resorting to an oxidizing agent.

Thus, a subject of the present invention is a naphthalimide dye corresponding to the compounds of general formula (I) and to the dimers of the compounds (I) corresponding to the following general formulae (II), (III) and (IV), and to their addition salts with an acid and their solvates:

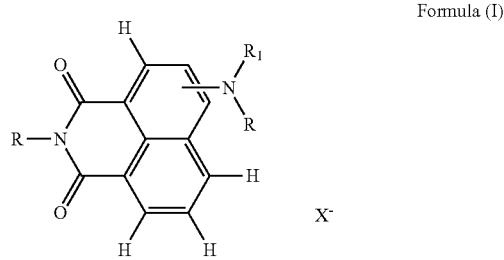

Formula (I)

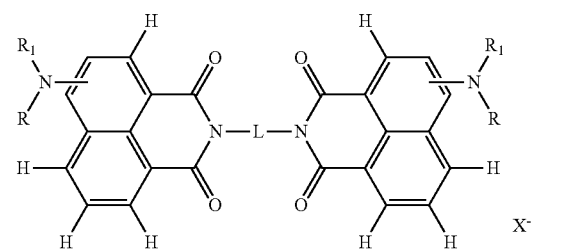

Formula (II)

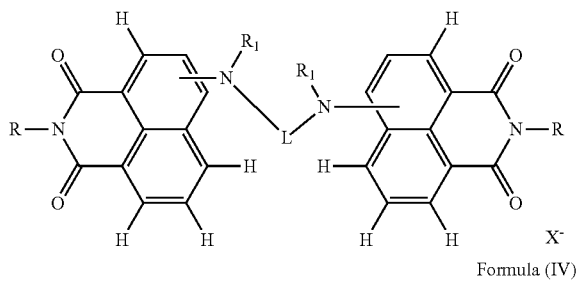

Formula (III)

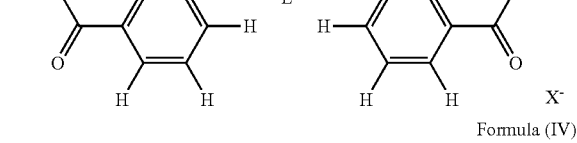

Formula (IV)

in which formulae (I) to (IV):

the radicals $R_1$, taken separately and independently of one another, represent a hydrogen atom; an optionally substituted $C_1$-$C_4$ alkyl radical, the radicals R, taken separately and independently of one another, represent a hydrogen atom; an aryl or arylalkyl radical, in which the aryl part is optionally substituted; an optionally substituted $C_1$-$C_8$, preferably $C_2$-$C_8$, alkyl radical that is optionally interrupted with one or more heteroatoms chosen from oxygen, nitrogen and sulphur, and that may be substituted with at least one group corresponding to the following formulae (a) and (b):

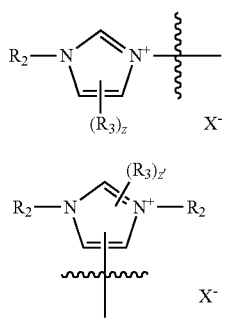

in which the radical $R_2$ represents an optionally substituted $C_1$-$C_6$ alkyl radical, the radical $R_3$ represents a halogen atom, an optionally substituted $C_1$-$C_6$ alkyl radical, a $C_1$-$C_4$ monohydroxyalkyl radical, a $C_1$-$C_4$ alkoxyl radical, a hydroxycarbonyl radical, a ($C_1$-$C_6$)alkylthio radical, or an amino radical disubstituted with a $C_1$-$C_4$ alkyl radical, z is an integer between 0 and 3 inclusive, z' is an integer between 0 and 2 inclusive, L is a cationic or non-cationic linker arm;

$X^-$ represents a counterion for ensuring the electroneutrality of the compounds of formulae (I) to (IV).

The naphthalimide dyes of the present application are cationic.

In a specific embodiment, at least one of the radicals R represents an optionally substituted $C_1$-$C_8$, preferably $C_2$-$C_8$, radical that is optionally interrupted with one or more heteroatoms chosen from oxygen, nitrogen and sulphur, and substituted with at least one group of formula (a) or (b) as defined above.

The dyes of the present invention make it possible to obtain dyes which are very chromatic and which inhibit good resistance with respect to outside agents, in particular shampoos. Moreover, the dyes of the present invention make it possible to obtain a lightening effect on dark keratin fibres, in particular keratin fibres with a tone depth of less than or equal 6, preferably less than or equal to 4, without having to resort to an oxidizing agent, it being possible for the fibres to be artificially or naturally coloured. When the use of an oxidizing agent is desired, for example in order to obtain greater bleaching, the dyes of the present invention exhibit good stability in an oxidizing medium.

The present application also relates to the use, as a direct dye, of at least one of the naphthalimide-type dyes that are subjects of the present application, for dyeing keratin fibres, and in particular human keratin fibres such as hair.

A subject of the present invention is, likewise, dye compositions comprising, in an appropriate dye medium, at least one of the dyes of formulae (I) to (IV), of their addition salts with an acid, or of their solvates.

The invention also relates to a process for the dyeing of keratin fibres, which comprises the application of the composition of the invention to keratin fibres for a period of time sufficient to obtain the desired colouration.

Finally, a subject of the invention is a multicompartment device comprising, in a first compartment, the composition according to the invention, and, in a second compartment, an oxidizing composition.

For the purpose of the present invention, and unless otherwise indicated:

An alkyl or alkylene radical or the alkyl or alkylene part of a radical is linear or branched, An alkyl or alkylene radical or the alkyl or alkylene part of a radical is said to be "substituted" when it comprises at least one substituent chosen from the following groups: hydroxyl, $C_1$-$C_4$ alkoxyl, $C_2$-$C_4$ (poly)hydroxyalkoxyl, amino, amino substituted with one or two identical or different $C_1$-$C_4$ alkyl groups optionally carrying at least one hydroxyl or $C_1$-$C_2$ alkoxyl group, it being possible for said alkyl radicals to form, with the nitrogen atom to which they are attached, a saturated or unsaturated, optionally aromatic, optionally substituted heterocycle comprising from 5 to 7 ring members, optionally comprising at least one other heteroatom which may or may not be different from nitrogen, an alkylcarbonylamino radical (R'CO—NR—) in which the radical R is a hydrogen atom, a $C_1$-$C_4$ alkyl radical, and the radical R' represents a $C_1$-$C_4$ alkyl radical, a phenyl radical;

an alkylsulphonyl radical (R—$SO_2$—) in which the radical R represents a $C_1$-$C_4$ alkyl radical, an alkylsulphinyl radical (R—SO—) in which the radical R represents a $C_1$-$C_4$ alkyl radical, an alkylcarbonyl radical (R—CO—) in which the radical R represents a $C_1$-$C_4$ alkyl radical.

A saturated or unsaturated, aromatic or non-aromatic (hetero)cyclic radical, or the saturated or unsaturated, aromatic or non-aromatic (hetero)cyclic part of a radical is said to be "substituted" when it comprises at least one substituent, preferably carried out by a carbon atom, chosen from:

an optionally substituted $C_1$-$C_{16}$, preferably $C_1$-$C_8$, alkyl radical;

a halogen atom such as chlorine, fluorine or bromine;

a hydroxyl group;

a $C_1$-$C_4$ alkoxyl radical; a $C_2$-$C_4$ (poly)hydroxyalkoxyl radical;

an amino radical;

an amino radical substituted with one or two identical or different $C_1$-$C_4$ alkyl radicals optionally carrying at least one hydroxyl, amino or $C_1$-$C_4$ (mono- or di-) alkylamino or $C_1$-$C_2$ alkoxyl group; it being possible for the two alkyl radicals to form, with the nitrogen atom to which they are attached, a heterocycle containing 1 to 3 heteroatoms, preferably 1 or 2 heteroatoms, chosen from N, O and S, preferably N, the heterocycle comprising from 5 to 7 ring members, and being saturated or unsaturated, aromatic or nonaromatic, and optionally substituted;

an alkylcarbonylamino radical (R'CO—NR—) in which the radical R is a hydrogen atom or a $C_1$-$C_4$ alkyl radical and the radical R' is a $C_1$-$C_2$ alkyl radical;

an aminocarbonyl radical ((R)$_2$N—CO—) in which the radicals R, which may or may not be identical, represent a hydrogen atom or a $C_1$-$C_4$ alkyl radical;

an alkylsulphonylamino or arylsulphonylamino (R'$SO_2$—NR—) radical in which the radical R represents a hydrogen atom or a $C_1$-$C_4$ alkyl radical and the radical R' represents a $C_1$-$C_4$ alkyl radical or a phenyl radical;

an aminosulphonyl radical ((R)$_2$N—$SO_2$—) in which the radicals R, which may or may not be identical, represent a hydrogen atom or a $C_1$-$C_4$ alkyl radical.

The compounds derived from formulae (II) and (III) are symmetric or dissymmetric. They are referred to as symmetric when a plane of symmetry perpendicular to the linker arm L exists. They are referred to as dissymmetric when no plane of symmetry perpendicular to the linker arm L exists.

In the following text, and unless otherwise indicated, the limits delimiting a range of values are included in this range.

As indicated above, a first subject of the invention consists of compounds corresponding to the abovementioned formulae (I) to (IV), their addition salts and their solvates.

Preferably, the compounds of formulae (I) to (IV) according to the present invention are such that:

the radicals $R_1$, which may or may not be identical, independently of one another represent a hydrogen atom, a $C_1$-$C_4$ linear alkyl radical optionally substituted with a hydroxyl group, a $C_1$-$C_2$ alkoxyl radical, a ($C_1$-$C_4$)dialkylamino radical, a ($C_1$-$C_3$)alkyl-carbonylamino radical or a ($C_1$-$C_2$)alkyl-sulphonylamino radical.

Even more preferably, the radicals $R_1$, which may be identical or different, independently of one another, represent:

a hydrogen atom;

a $C_1$-$C_4$ alkyl radical, for example methyl or ethyl.

In a first variant, L is a non-cationic linker arm that connects the two identical or different naphthalimide-type chromophores. According to this variant, L represents:

a covalent bond;

an optionally substituted $C_2$-$C_{40}$, preferably $C_2$-$C_{20}$ alkylene radical optionally interrupted with an optionally substituted, optionally condensed, saturated or unsaturated, aromatic or nonaromatic (hetero)cycle comprising from 3 to 7 ring members; said alkyl radical being optionally interrupted with one or more heteroatoms or groups comprising at least one heteroatom, preferably oxygen, nitrogen, —CO—, —SO—, —SO$_2$— or combinations thereof; the linker arm L comprising no azo, nitro, nitroso or peroxo bond;

an optionally substituted phenyl radical.

According to this variant, by way of examples of a non-cationic linker arm L, mention may be made of linker arms of alkylene type, such as ethylene, linear or branched propylene, linear or branched butylene, linear or branched pentylene or linear or branched hexylene radicals, optionally substituted and/or interrupted as indicated above.

These substituents, which may be identical or different, are preferably chosen from hydroxyl, $C_1$-$C_2$ alkoxyl, ($C_1$-$C_2$)dialkylamino, ($C_1$-$C_4$)alkylcarbonyl and ($C_1$-$C_4$)alkyl-sulphonyl groups.

By way of preferred examples of a saturated or unsaturated, aromatic or non-aromatic ring or heterocycle that interrupt the alkyl radical of the linker arm L, mention may be made of phenylene, naphthalene, phenanthrylene, triazinyl, pyrimidinyl, pyridinyl, pyridazinyl, quinoxalinyl or cyclohexyl radicals.

More particularly, the following radicals L are suitable:

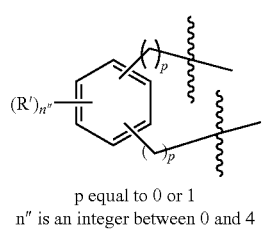

p equal to 0 or 1
n" is an integer between 0 and 4

—($C_nH_{2n}$)—

2 < n < 19

—($C_nH_{2n}$)$_2$—X$^-$

0 < n < 10
X = NH, NR$_4$, O, SO, SO$_2$

-continued

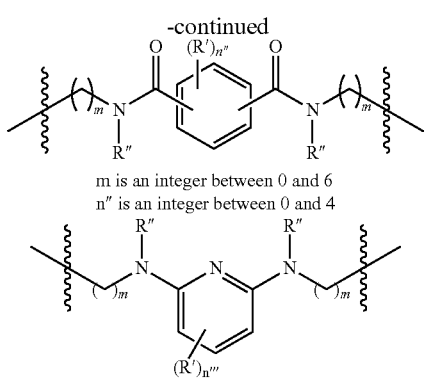

m is an integer between 0 and 6
n" is an integer between 0 and 4 m is an integer between 0 and 6
n''' is an integer between 0 and 3 in which formulae:

R' has the same definition as $R_1$;

R", which are identical, represent a hydrogen or a $C_1$-$C_4$ alkyl radical;

$R_4$ represents a hydrogen atom, or a $C_1$-$C_8$ alkyl radical optionally substituted with one or more radicals, which may be identical or different, chosen from the groups hydroxyl, $C_1$-$C_2$ alkoxyl, $C_2$-$C_4$ (poly)hydroxyalkoxyl, amino, $C_1$-$C_2$ (di-)alkylamino or aryl, which is optionally substituted.

By way of examples of specific radicals L, mention may also be made of:

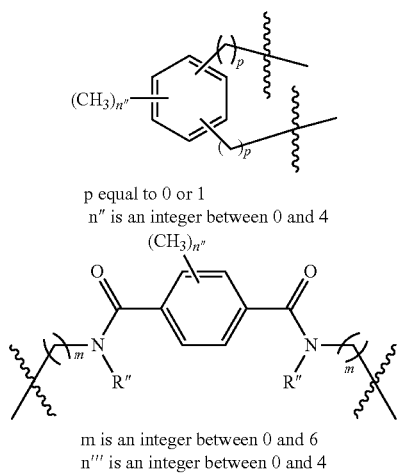

p equal to 0 or 1
n" is an integer between 0 and 4 m is an integer between 0 and 6
n''' is an integer between 0 and 4

According to a second variant, L represents a cationic linker arm. According to this variant, the cationic linker arm L advantageously represents a $C_2$-$C_{20}$ alkylene radical interrupted with at least one group corresponding to the following formulae:

(a')

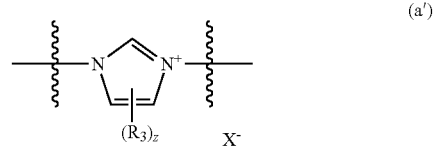

-continued

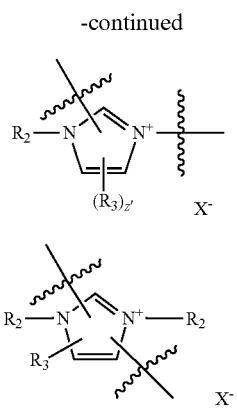

in which:
R$_2$ and R$_3$, taken separately and independently of one another, have the same meaning as above,
z and z' have the same meaning as above,
X$^-$ is as defined above.

The cationic alkylene radical thus defined may be optionally interrupted with one or more heteroatoms or groups comprising at least one heteroatom, or combinations thereof, such as, for example, oxygen, nitrogen, a —CO— group, an —SO— group or an —SO$_2$— group; with the proviso that there is no azo, nitro, nitroso or peroxo group or bond in the linker arm L. It may also be optionally substituted in particular with one of more radicals chosen from the following radicals: hydroxyl, C$_1$-C$_2$ alkoxyl, C$_2$-C$_4$ (poly)hydroxyalkoxyl, amino substituted with one or more C$_1$-C$_2$ alkyl groups optionally carrying at least one hydroxyl group.

According to a specific embodiment of formulae (a), (b), (b') and (c'), the radicals R$_2$, taken separately and independently of one another, represent a C$_1$-C$_6$ alkyl radical optionally substituted with a hydroxyl group, a C$_1$-C$_2$ alkoxyl group, a hydroxycarbonyl group, a (C$_1$-C$_6$)alkylthio group, or an amino group disubstituted with a (C$_1$-C$_4$)alkyl radical.

According to a specific embodiment of formulae (a), (b), (b') and (c'), R$_2$ represents an alkyl radical such as methyl or ethyl, a hydroxyalkyl radical such as 2-hydroxyethyl, an alkoxyalkyl radical such as 2-methoxyethyl, a hydroxycarbonylalkyl radical such as 3-hydroxycarbonylpropyl, or a dialkylaminoalkyl radical such as 3-N,N-dimethylaminopropyl.

According to a specific embodiment of formulae (a), (b), (a'), (b') and (c'), R$_3$ represents a halogen atom chosen from chlorine and fluorine, a C$_1$-C$_6$ alkyl radical, a C$_1$-C$_4$ monohydroxyalkyl radical, a C$_1$-C$_4$ alkoxyl radical, a hydroxycarbonyl radical, a (C$_1$-C$_6$)alkylthio radical, or an amino radical disubstituted with a (C$_1$-C$_4$)alkyl radical. By way of example of radicals R$_3$, mention may be made of a chlorine atom, a methyl, an ethyl, a 2-hydroxyethyl, a methoxy, a hydroxycarbonyl or a dimethylamino.

According to a variant of formulae (a), (b), (a') and (b'), z and z' are equal to 0.

According to a specific embodiment, the radicals R, taken separately and independently of one another, represent a hydrogen atom; a C$_1$-C$_6$, preferably C$_2$-C$_6$, alkyl radical optionally substituted with one or more groups, which may be identical or different, preferably chosen from hydroxyl and C$_1$-C$_2$ alkoxyl substituents, and optionally substituted with at least one group corresponding to formula (a) as defined above; an aryl or arylalkyl radical, such as phenyl or benzyl, the aryl part being optionally substituted with one or more groups, which may be identical or different, preferably chosen from a chlorine atom, an amino group, a hydroxyl group; a C$_1$-C$_2$ alkoxyl group, and an amino group mono- or disubstituted with two C$_1$-C$_4$ alkyl radicals, which may be identical or different, optionally carrying at least one hydroxyl group.

In accordance with a preferred embodiment of the invention, the radicals R, which may be identical or different, independently of one another, represent a hydrogen atom; a C$_1$-C$_3$ alkyl radical such as methyl or ethyl, a hydroxyalkyl radical such as 2-hydroxy-ethyl, an alkoxyalkyl radical such as 2-methoxyethyl, a C$_1$-C$_3$ alkyl radical substituted with at least one group corresponding to the following formula (a"), a benzyl radical optionally substituted with one or more radicals, which may be identical or different, chosen from the groups hydroxyl, alkoxyl such as methoxy, amino, (di)alkylamino such as dimethylamino, (di)(hydroxyalkyl)amino such as (di)(2-hydroxyethyl)amino.

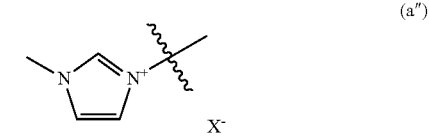

In formulae (I) to (IV), X$^-$ represents an organic or inorganic counterion or a mixture of organic or inorganic counterions, which makes it possible to equilibrate the charge(s) of the compounds of formulae (I) to (IV). X$^-$ is, for example, chosen from a halide such as chloride, bromide, fluoride, iodide; a hydroxide; a sulphate; a hydrogen sulphate; an alkyl sulphate for which the linear or branched alkyl part is C$_1$-C$_6$, such as the methyl sulphate or ethyl sulphate ion; carbonates and hydrogen carbonates; carboxylic acid salts such as formate, acetate, citrate, tartrate, oxalate; alkylsulphonates for which the linear or branched alkyl part is C$_1$-C$_6$, such as the methylsulphonate ion; arylsulphonates for which the aryl, preferably phenyl, part is optionally substituted with one or more C$_1$-C$_4$ alkyl radicals, such as, for example, 4-toluylsulphonate; alkylsulphonyls such as mesylate.

The addition salts with an acid of the compounds of formulae (I) to (IV) may, by way of example, be addition salts with an organic or inorganic acid, such as hydrochloric acid, hydrobromic acid, sulphuric acid or alkylsulphonic or phenylsulphonic acids, such as p-toluenesulphonic acid or methylsulphonic acid.

The solvates of the compounds of formulae (I) to (IV) represent the hydrates of such compounds and the association of a compound of formulae (I) to (IV) with a linear or branched C$_1$-C$_4$ alcohol, such as methanol, ethanol, isopropanol or n-propanol.

In accordance with a specific embodiment of the invention, the compounds corresponding to formulae (I), (II), (III) and (IV), and also their resonance forms and/or their addition salts with an acid and/or their solvates are chosen from the following compounds:

The 3-methyl-1-{3-[(2-methyl-1,3-dioxo-2,3-dihydro-1H-benzo[de]isoquinolin-6-yl)amino]propyl}-1H-imidazol-3-ium salt

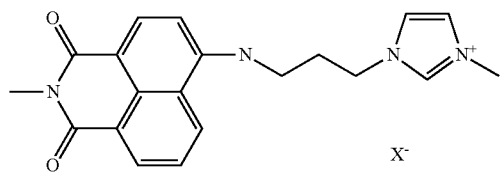

The 1-{3-[6-[(2-hydroxyethyl)amino]-1,3-dioxo-1H-benzo[de]isoquinolin-2(3H)-yl]propyl}-3-methyl-1H-imidazol-3-ium salt

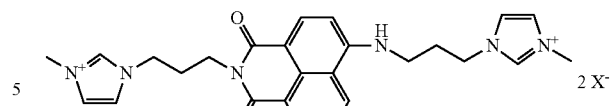

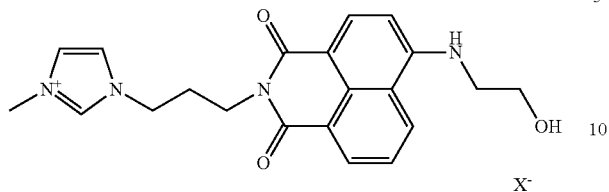

The 3-methyl-1-{3-[(6-{[3-(3-methyl-1H-imidazol-3-ium-1-yl)propyl]amino}-1,3-dioxo-1H-benzo[de]isoquinolin-2(3H)-yl]propyl}-1H-imidazol-3-ium salt:

The 3-{5-[(2-ethyl-1,3-dioxo-2,3-dihydro-1H-benzo[de]isoquinolin-6-yl)amino]-pentyl}-1-{3-[(2-ethyl-1,3-dioxo-2,3-dihydro-1H-benzo[de]isoquinolin-6-yl)amino]-propyl}-1H-imidazol-3-ium salt

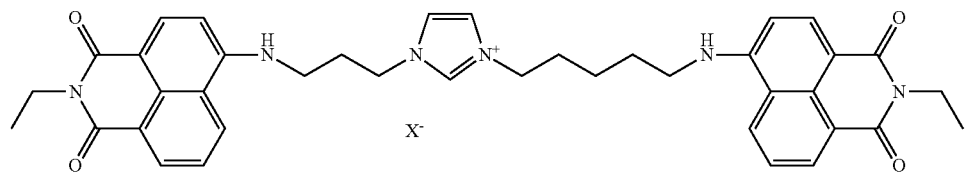

The 3,3'-butane-1,4-diylbis(1-{5-[(2-ethyl-1,3-dioxo-2,3-dihydro-1H-benzo[de]isoquinolin-6-yl)amino]pentyl}-1H-imidazol-3-ium salt

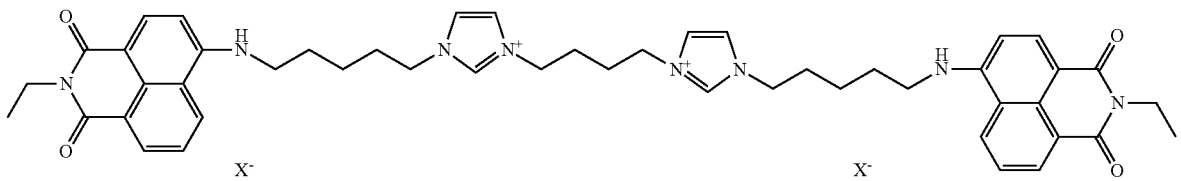

The 3-{5-[(2-ethyl-1,3-dioxo-2,3-dihydro-1H-benzo[de]isoquinolin-6-yl)amino]-pentyl}-1-[3-({2-[3-(1-methyl-1H-imidazol-3-ium-3-yl)propyl]-1,3-dioxo-2,3-dihydro-1H-benzo[de]isoquinolin-6-yl}amino)propyl]-1H-imidazol-3-ium salt

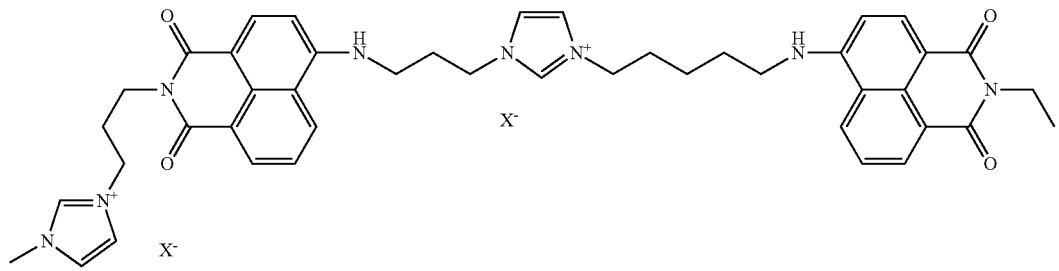

The 1-{5-[(2-ethyl-1,3-dioxo-2,3-dihydro-1H-benzo[de]isoquinolin-6-yl)amino]-pentyl}-3-(4-{1-[5-({2-[3-(1-methyl-1H-imidazol-3-ium-3-yl)propyl]-1,3-dioxo-2,3-dihydro-1H-benzo[de]isoquinolin-6-yl}amino)pentyl]-1H-imidazol-3-ium-3-yl}butyl)-1H-imidazol-3-ium salt

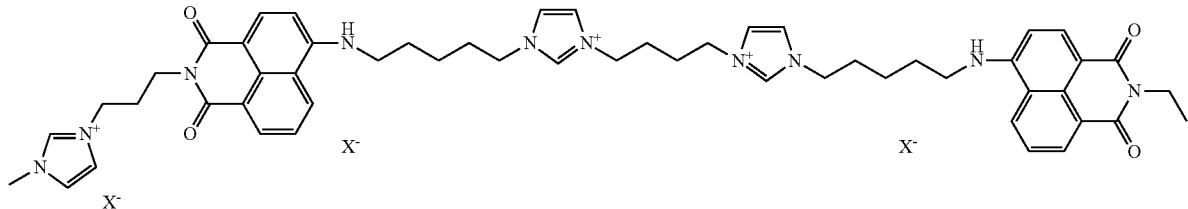

The 1-methyl-3-{3-[6-[(3-{3-[5-({2-[3-(1-methyl-1H-imidazol-3-ium-3-yl)-propyl]-1,3-dioxo-2,3-dihydro-1H-benzo[de]isoquinolin-6-yl}amino)pentyl]-1H-imidazol-3-ium-1-yl}propyl)amino]-1,3-dioxo-1H-benzo[de]isoquinolin-2(3H)-yl]propyl}-1H-imidazol-3-ium salt

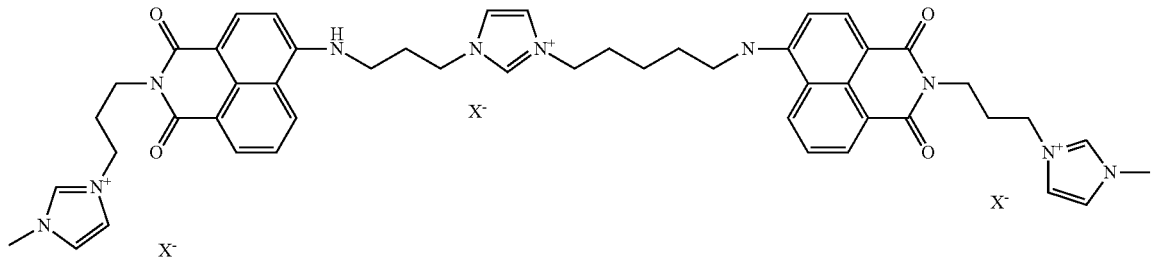

The 3,3'-butane-1,4-diylbis{1-[5-({2-[3-(1-methyl-1H-imidazol-3-ium-3-yl)-propyl]-1,3-dioxo-2,3-dihydro-1H-benzo[de]isoquinolin-6-yl}amino)pentyl]-1H-imidazol-3-ium} salt

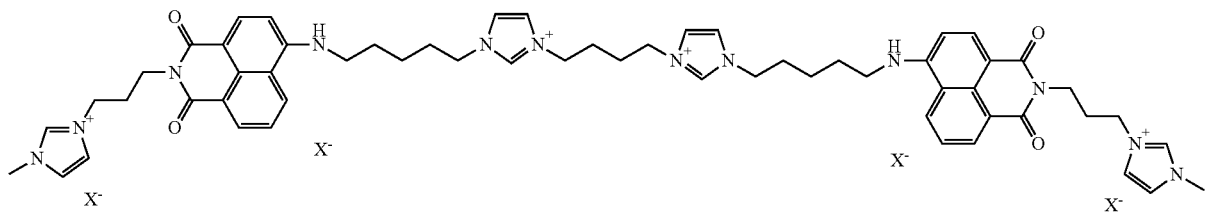

The 1-methyl-3-[3-({2-[3-(3-{5-[6-{[3-(1-methyl-1H-imidazol-3-ium-3-yl)-propyl]amino}-1,3-dioxo-1H-benzo[de]isoquinolin-2(3H)-yl]pentyl}-1H-imidazol-3-ium-1-yl)propyl]-1,3-dioxo-2,3-dihydro-1H-benzo[de]isoquinolin-6-yl}amino)propyl]-1H-imidazol-3-ium salt

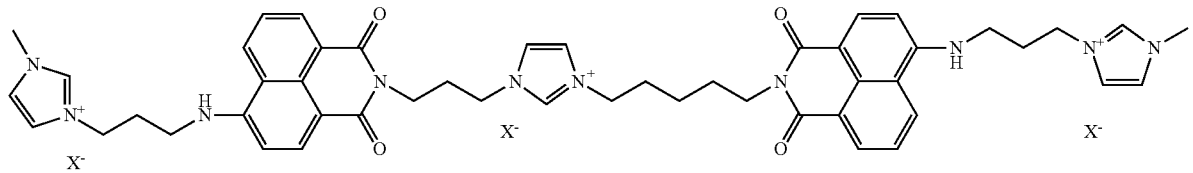

The 3-{6-[6-[bis(2-hydroxyethyl)amino]-1,3-dioxo-1H-benzo[de]isoquinolin-2(3H)-yl]hexyl}-1-{3-[(2-methyl-1,3-dioxo-2,3-dihydro-1H-benzo[de]isoquinolin-6-yl)-amino]propyl}-1H-imidazol-3-ium salt

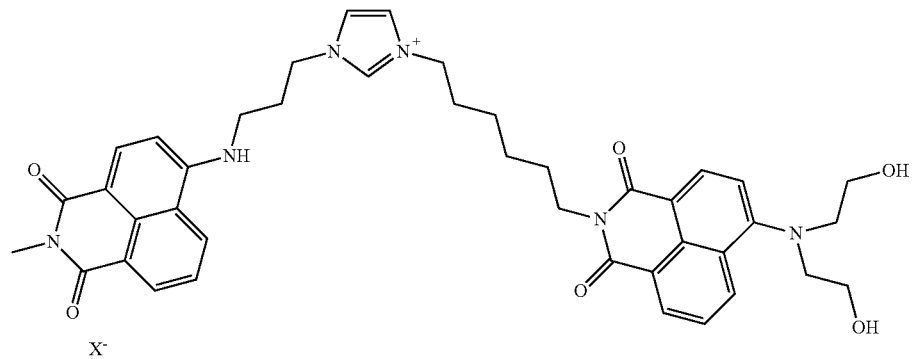

The 3-methyl-1-[3-({2-[6-(1-{3-[(2-methyl-1,3-dioxo-2,3-dihydro-1H-benzo-[de]isoquinolin-6-yl)amino]propyl}-1H-imidazol-3-ium-3-yl)hexyl]-1,3-dioxo-2,3-dihydro-1H-benzo[de]isoquinolin-6-yl}amino)propyl]-1H-imidazol-3-ium salt

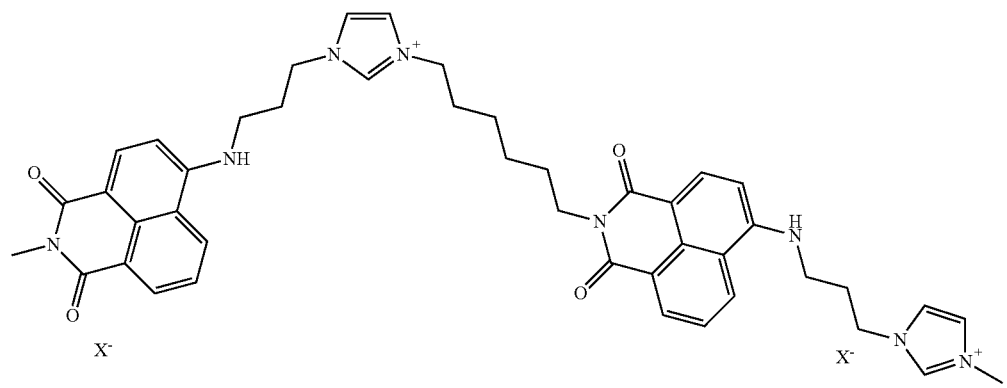

The 1-methyl-3-{3-[6-{[3-(3-{6-[6-{[3-(3-methyl-1H-imidazol-3-ium-1-yl)-propyl]amino}-1,3-dioxo-1H-benzo[de]isoquinolin-2(3H)-yl]hexyl}-1H-imidazol-3-ium-1-yl)propyl]amino}-1,3-dioxo-1H-benzo[de]isoquinolin-2(3H)-yl]propyl}-1H-imidazol-3-ium salt

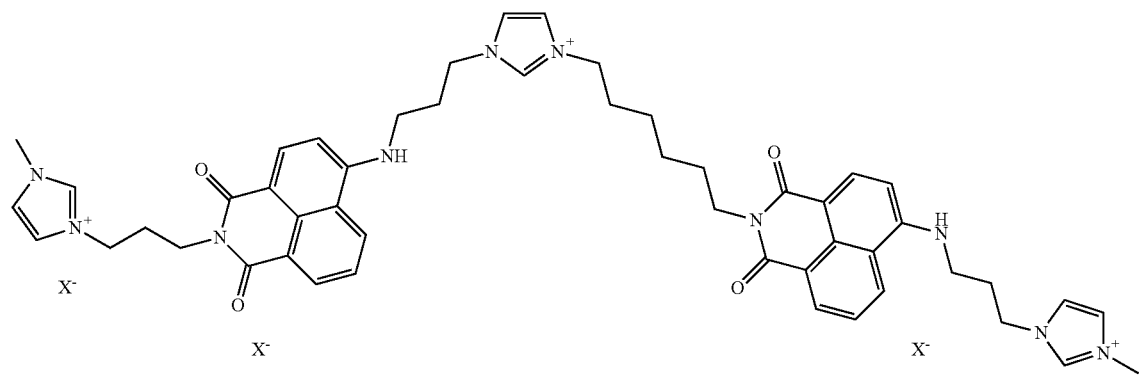

The 3-methyl-1-[3-({2-[6-(1-{6-[6-{[3-(1-methyl-1H-imidazol-3-ium-3-yl)-propyl]amino}-1,3-dioxo-1H-benzo[de]isoquinolin-2(3H)-yl]hexyl}-1H-imidazol-3-ium-3-yl)hexyl]-1,3-dioxo-2,3-dihydro-1H-benzo[de]isoquinolin-6-yl}amino)propyl]-1H-imidazol-3-ium salt

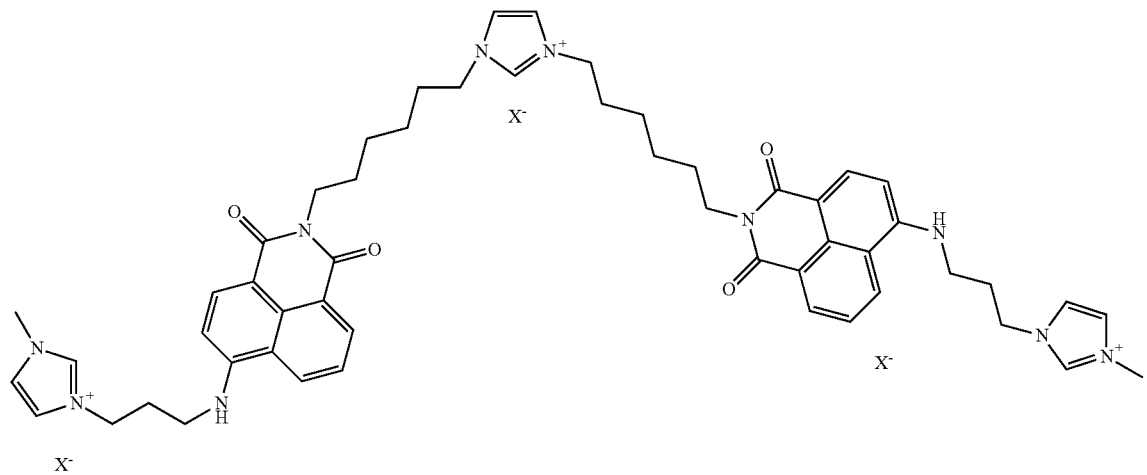

According to a particular embodiment of the invention, the compounds of formula (I) correspond to the following formula:

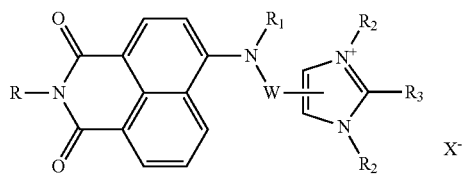

in which

W represents a $C_1$-$C_8$ alkyl radical, preferably $C_2$-$C_8$, and even more preferably, $C_2$-$C_4$, R, $R_1$, $R_2$, $R_3$ and $X^-$ are as defined above.

Preferably, they correspond to the following formula:

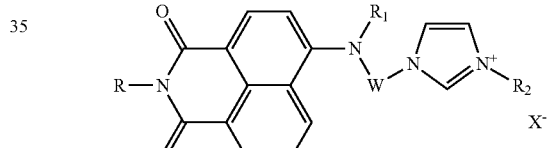

in which

W represents a $C_1$-$C_8$ alkyl radical, preferably $C_2$-$C_8$, and even more preferably, $C_2$-$C_4$, R, $R_1$, $R_2$ and $X^-$ are as defined above.

According to a specific embodiment of the invention, the compounds of formula (II) correspond to the following formula:

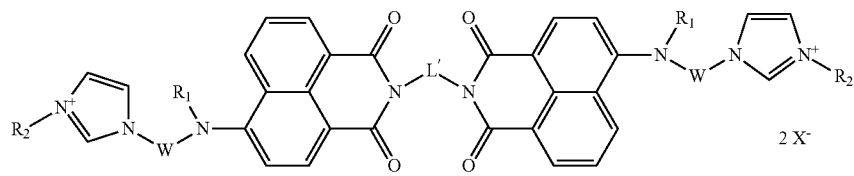

in which
W represents a $C_1$-$C_8$ radical, preferably $C_2$-$C_8$, and even more preferably, $C_2$-$C_4$,
$R_1$, $R_2$ and $X^-$ are as defined above,
L' is defined as L.

According to a specific embodiment of the invention, the compounds of formula (III) correspond to the following formula:

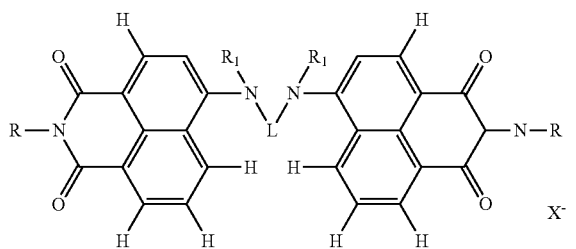

in which R, $R_1$ and L are as defined above.

According to a specific embodiment of the invention, the compounds of formula (IV) correspond to the following formula:

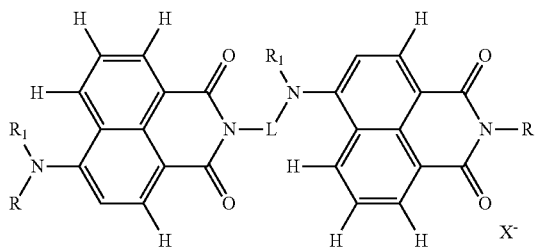

in which R, $R_1$, L and $X^-$ are as defined above.

The compounds represented above can in particular be obtained using the preparation processes described, for example, in the documents:

Konstantinova, T.; Spirieva, A.; Petkova, T. Dyes and Pigments 2000, 45, 125-129.

Gunnlaugsson, T.; Kruger, P. E.; Clive Lee, T.; Parkesh, R.; Pfeffer, F. M.; Hussey, G. M. Tetrahedron Lett., 2003, 44, 6575-6578.

Shepard, E. R.; Shonle, H. A. J. Am. Chem. Soc. 1947, 69, 2269-2270.

The composition according to the invention may contain one or more naphthalimide-type compounds of formula (I), (II), (III) or (IV), or one or more of their addition salts with an acid and/or solvates, as defined above, mixtures of these compounds then being possible in any relative proportions.

The composition according to the present application generally comprises from 0.001% to 10%, preferably 0.01% to 10% by weight of one or more naphthalimide-type compounds of formula (I), (II), (III) or (IV), or one or more of their addition salts with an acid and/or solvates, relative to the total weight of the composition.

The dye composition in accordance with the invention can also contain one or more additional direct dyes other than the direct dyes of formula (I), (II), (III) or (IV), it being possible for these additional direct dyes to be in particular chosen from neutral, acidic or cationic nitrobenzene dyes, neutral, acidic or cationic azo direct dyes, neutral, acidic or cationic quinone, and in particular anthraquinone, direct dyes, azine direct dyes, triarylmethane direct dyes, indoamine direct dyes, tetranzapentamethine-type dyes and natural direct dyes.

Among the benzene direct dyes that can be used according to the invention, mention may be made, in a nonlimiting manner, of the following compounds:

1,4-di amino-2-nitrobenzene,
1-amino-2 nitro-4-β-hydroxyethylaminobenzene
1-amino-2 nitro-4-bis(β-hydroxyethyl)aminobenzene
1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene
1-hydroxy-4-β-hydroxyethylamino-3-nitrobenzene.

Among the azo direct dyes that can be used according to the invention, mention may be made of the cationic azo dyes described in patent applications WO 95/15144, WO 95/01772 and EP-A-714 954.

Among these compounds, mention may most particularly be made of the following dyes:

1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]pyridinium methyl sulphate.

Among azo direct dyes, mention may also be made of the following dyes, described in the COLOUR INDEX INTERNATIONAL 3rd edition:

Disperse Red 17
Acid Yellow 9
Acid Black 1
Basic Red 22
Basic Red 76
Basic Yellow 57
Basic Brown 16
Acid Yellow 36
Acid Orange 7
Acid Red 33

Acid Red 35
Basic Brown 17
Acid Yellow 23
Acid Orange 24
Disperse Black 9.

Mention may also be made of 1-(4'-aminodiphenylazo)-2-methyl-4-bis-(β-hydroxyethyl)aminobenzene and 4-hydroxy-3-(2-methoxyphenylazo)-1-naphthalene-sulphonic acid.

Among the quinone direct dyes, mention may be made of the following dyes:
Disperse Red 15
Solvent Violet 13
Acid Violet 43
Disperse Violet 1
Disperse Violet 4
Disperse Blue 1
Disperse Violet 8
Disperse Blue 3
Disperse Red 11
Acid Blue 62
Disperse Blue 7
Basic Blue 22
Disperse Violet 15
Basic Blue 99
and also the following compounds:
1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine dyes, mention may be made of the following compounds:
Basic Blue 17
Basic Red 2.

Among the triarylmethane dyes that can be used according to the invention, mention may be made of the following compounds:
Basic Green 1
Acid blue 9
Basic Violet 3
Basic Violet 14
Basic Blue 7
Acid Violet 49
Basic Blue 26
Acid Blue 7.

Among the indoamine dyes that can be used according to the invention, mention may be made of the following compounds:
2-β-hydroxyethylamino-5-[bis(β-4'-hydroxyethyl)amino]anilino-1,4-benzo-quinone
2-β-hydroxyethlyamino-5-(2'-methoxy-4'-amino)anilino-1,4-benzoquinone
3-N(2'-chloro-4'-hydroxy)phenylacetylamino-6-methoxy-1,4-benzoquinoneimine
3-N(3'-chloro-4'-methylamino)phenylureido-6-methyl-1,4-benzoquinoneimine
3-[4'-N-(ethylcarbamylmethyl)amino]phenylureido-6-methyl-1,4-benzo-quinoneimine.

Among the tetraazapentamethine-type dyes that can be used according to the invention, mention may be made of the following compounds given in the table below. An representing, in general, an organic or inorganic anion, for example chosen from a halide such as a chloride, a bromide, a fluoride or an iodide; a hydroxide; a sulphate; a hydrogen sulphate; a ($C_1$-$C_6$)alkyl sulphate such as, for example, a methyl sulphate or an ethyl sulphate; an acetate; a tartrate; an oxalate; a ($C_1$-$C_6$)alkylsulphonate such as methylsulphonate; an arylsulphonate which is unsubstituted or substituted with a $C_1$-$C_4$ alkyl radical, such as, for example, a 4-toluylsulphonate. An is preferably a chloride; a methyl sulphate:

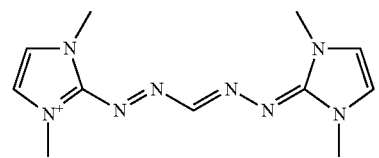

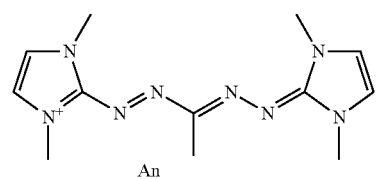

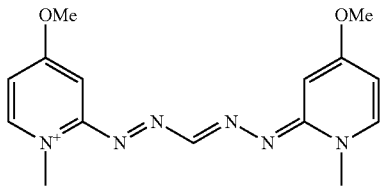

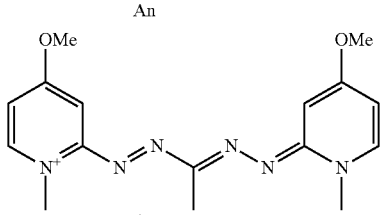

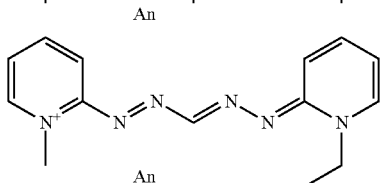

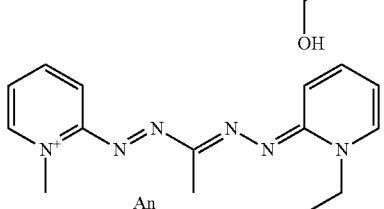

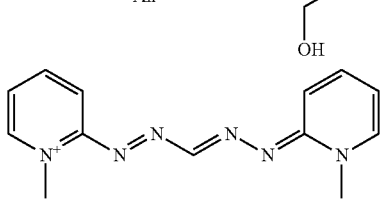

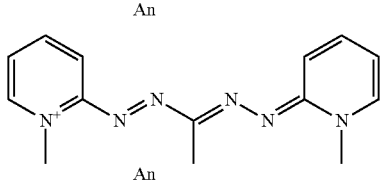

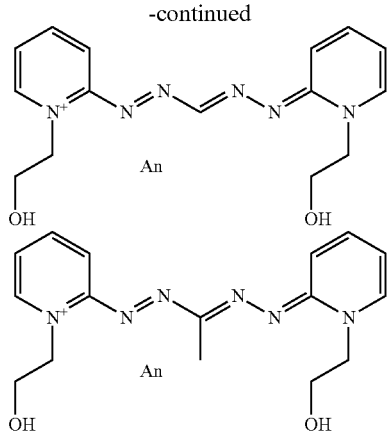

Among the natural direct dyes that can be used according to the invention, mention may be made of lawsone, juglone, alizarin, purpurin, carminic acid, kermesic acid, purpurogallin, protocatechaldehyde, indigo, isatin, curcumin, spinulosine and apigenidine. Extracts or decoctions containing these natural dyes, and in particular henna-based poultices or extracts, may also be used.

The additional direct dye(s) preferably represent(s) from approximately 0.001% to 20% by weight of the total weight of the ready-to-use composition, and even more preferably from approximately 0.005% to 10% by weight.

The composition of the present invention may also comprise one or more oxidation dye precursors: one or more oxidation bases and/or one or more couplers.

By way of example, the oxidation bases are chosen from phenylenediamines, bisphenylalkylenediamines, para-aminophenols, ortho-aminophenols, heterocyclic bases other than heterocyclic para-phenylenediamines, and addition salts thereof.

Among the para-phenylenediamines, mention may be made, by way of example, of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylene-diamine, 4-amino N,N-diethyl-3-methylaniline, N,N-bis(β-hydroxyethyl)-para-phenylene-diamine, 4-N,N-bis(β-hydroxyethyl)amino-2-methylaniline, 4-N,N-bis(β-hydroxyethyl)-amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylene-diamine, 4-aminophenylpyrrolidine, 2-thienyl-para-phenylenediamine, 2-β-hydroxy-ethylamino-5-aminotoluene, 3-hydroxy-1-(4'-aminophenyl)pyrrolidine, and their addition salts with an acid.

Among the para-phenylenediamines mentioned above, para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylene-diamine, 2-β-acetylaminoethyloxy-para-phenylenediamine, and their addition salts with an acid, are particularly preferred.

Among the bisphenylalkylenediamines, mention may be made, by way of example, of N,N'-bis(β-hydroxyethyl)-N, N'-bis-(4'-aminophenyl)-1,3-diaminopropanol, N,N'-bis(β-hydroxyethyl)-N,N'-bis-(4'-aminophenypethylenediamine, N,N'-bis-(4-amino-phenyl)tetramethylenediamine, N,N'-bis(β-hydroxyethyl)-N,N'-bis-(4-aminophenyptetramethylenediamine, N,N'-bis-(4-methylaminophenyl)tetramethylenediamine, N,N'-bis-(ethyl)-N,N'-bis-(4'-amino-3'-methylphenypethylenediamine, 1,8-bis-(2,5-diaminophenoxy)-3,6-dioxaoctane, and their addition salts.

Among the para-aminophenols, mention may be made, by way of example of, para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and their addition salts with an acid.

Among the ortho-aminophenols, mention may be made, by way of example, of 2-aminophenol, 2-amino-5-methylphenol, 2-amino-6-methylphenol, 5-acetamido-2-aminophenol, and their addition salts.

Among the heterocyclic bases, mention may be made, by way of example, of pyridine derivatives, pyrimidine derivatives and pyrazole derivatives.

Among the pyridine derivatives, mention may be made of the compounds described, for example, in patents GB-A-1 026 978 and GB-A-1 153 196, such as 2,5-diaminopyridine, 2-(4-methoxyphenyl)amino-3-aminopyridine, 3,4-diaminopyridine, and their addition salts.

Other pyridine oxidation bases that can be used in the present invention are the 3-aminopyrazolo[1,5-a]pyridine oxidation bases, or their addition salts, described for example in patent application FR-A-2 801 308. By way of example, mention may be made of pyrazolo[1,5-a]pyridin-3-ylamine; 2-acetylaminopyrazolo[1,5-a]pyridin-3-ylamine; 2-morpholin-4-ylpyrazolo[1,5-a]pyridin-3-ylamine; 3-aminopyrazolo[1,5-a]pyridin-2-carboxylic acid; 2-methoxypyrazolo[1,5-a]pyridin-3-yl amine; (3-aminopyrazolo-[1,5-a]pyridin-7-yl)methanol; 2-(3-aminopyrazolo[1,5-a]pyridin-5-yl)ethanol; 2-(3-amino-pyrazolo[1,5-a]pyridin-7-yl)ethanol; (3-aminopyrazolo[1,5-a]pyridin-2-yl)methanol; 3,6-diaminopyrazolo[1,5-a]pyridine; 3,4-diaminopyrazolo[1,5-a]pyridine; pyrazolo-[1,5-a]pyridine-3,7-diamine; 7-morpholin-4-ylpyrazolo[1,5-a]pyridin-3-ylamine; pyrazolo-[1,5-a]pyridine-3,5-diamine; 5-morpholin-4-ylpyrazolo[1,5-a]pyridin-3-ylamine; 2-[(3-aminopyrazolo[1,5-a]pyridin-5-yl)-(2-hydroxyethyl)amino]ethanol; 2-[(3-amino-pyrazolo[1,5-a]pyridin-7-yl)-(2-hydroxyethyl)amino]ethanol; 3-aminopyrazolo[1,5-a]pyridin-5-ol; 3-aminopyrazolo[1,5-a]pyridin-4-ol; 3-aminopyrazolo[1,5-a]pyridin-6-ol; 3-amino-pyrazolo[1,5-a]pyridin-7-ol; and also their addition salts.

Among the pyrimidine derivatives, mention may be made of the compounds described, for example, in patents DE-A-23 59 399; JP 88-169571; EP-A-0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-di-aminopyrimidine, 2,5,6-triaminopyrimidine, their addition salts and their tautomeric forms, when a tautomeric equilibrium exists.

Among the pyrazole derivatives, mention may be made of the compounds described in patents DE-A-38 43 892 and DE-A-41 33 957 and patent applications WO 94/08969, WO 94/08970, FR-A-2 733 749 and DE-A-195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their addition salts.

The oxidation base(s) present in the composition of the invention is (are) in general present in amounts ranging from approximately 0.001% to 20% by weight of the total weight of the dye composition, preferably ranging from 0.005% to 6% by weight.

The composition according to the invention preferably contains one or more couplers conventionally used for dyeing keratin fibres. Among these couplers, mention may in particular be made of meta-phenylenediamines, meta-diphenols, naphthalene couplers, heterocyclic couplers, and their addition salts.

By way of example, mention may be made of 1,3-dihydroxybenzene, 1,3-dihydroxy-2-methylbenzene, 4-chloro-1,3-dihydroxybenzene, 2,4-diamino-1-(β-hydroxy-ethyloxy)benzene, 2-amino-4-(β-hydroxyethylamino)-1-methoxybenzene, 1,3-diaminobenzene, 1,3-bis-(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and their addition salts.

In the composition of the present invention, the coupler(s) is (are) generally present in an amount ranging from approximately 0.001% to 20% by weight of the total weight of the dye composition, preferably ranging from 0.005% to 6%.

In general, the addition salts of the oxidation bases and of the couplers that can be used in the context of the invention are in particular chosen from addition salts with an acid such as hydrochlorides, hydrobromides, sulphates, citrates, succinates, tartrates, lactates, tosylates, benzenesulphonates, phosphates and acetates, and addition salts with a base such as sodium hydroxide, potassium hydroxide, ammonia, amines or alkanolamines.

The medium suitable for dyeing, also called dye support, is in particular suitable for dyeing keratin fibres such as the hair. Such a medium is a cosmetic medium generally consisting of water or of a mixture of water and of at least one organic solvent for solubilizing the compounds that would not be sufficiently soluble in water. As organic solvent, mention may, for example, be made of $C_1$-$C_4$ lower alcohols such as ethanol and isopropanol; polyols and polyol ethers such as 2-butoxyethanol, propylene glycol, glycerol, propylene glycol monomethyl ether, diethylene glycol monoethyl ether and diethylene glycol monomethyl ether; and also aromatic alcohols such as benzyl alcohol or phenoxyethanol, and mixtures thereof.

The solvents are present in proportions of preferably between approximately 1% and 40% by weight, and even more preferably between approximately 5% and 30% by weight, relative to the total weight of the dye composition.

The dye compositions in accordance with the invention may also contain various adjuvants conventionally used in compositions for dyeing the hair, such as anionic, cationic, non-ionic, amphoteric or zwitterionic surfactants, or mixtures thereof, anionic, cationic, non-ionic, amphoteric or zwitterionic polymers, or mixtures thereof, inorganic or organic thickeners, and in particular anionic, cationic, non-ionic and amphoteric polymeric associative thickeners, antioxidants, penetrating agents, sequestering agents, fragrances, buffers, dispersants, conditioning agents such as, for example, volatile or non-volatile, modified or non-modified silicones, film-forming agents, ceramides, preserving agents or opacifiers.

The adjuvants above are in general present in amounts, for each of them, ranging from 0.01% to 20% by weight relative to the weight of the composition.

According to one variant, the composition of the invention comprises an oxidizing agent in order to obtain lightening of the fibres. The oxidizing agents conventionally used for the oxidation dyeing of keratin fibres are, for example, hydrogen peroxide, urea peroxide, alkali metal bromates, persalts such as perborates and persulphates, peracids and oxidase enzymes, among which mention may be made of peroxidases, 2-electron oxidoreductases such as uricases and 4-electron oxigenases such as laccases. According to a specific embodiment, the composition contains an oxidizing agent of peroxide type and/or an oxidizing agent of persalt type, for example a mixture of hydrogen peroxide and persulphate, hydrogen peroxide alone or persulphate alone.

Of course, those skilled in the art will take care to select this or these optional additional compound(s) in such a way that the advantageous properties intrinsically associated with the oxidation dyeing composition in accordance with the invention are not, or are not substantially, impaired by the envisaged addition(s).

The pH of the dye composition in accordance with the invention is generally between approximately 3 and 12, and preferably between approximately 5 and 11. It can be adjusted to the desired value by means of acidifying or basifying agents normally used in the dyeing of keratin fibres, or alternatively by means of conventional buffer systems.

Among the acidifying agents, mention may, by way of example, be made of inorganic or organic acids such as hydrochloric acid, ortho-phosphoric acid, sulphuric acid, carboxylic acids such as acetic acid, tartaric acid, citric acid, lactic acid, or sulphonic acids.

Among the basifying agents, mention may, by way of example, be made of aqueous ammonia, alkali metal carbonates, alkanolamines such as mono-, di- and triethanolamines and derivatives thereof, sodium hydroxide, potassium hydroxide and the compounds of following formula (II):

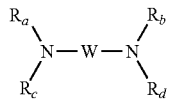

in which W is a propylene residue optionally substituted with a hydroxyl group or a $C_1$-$C_4$ alkyl radical; $R_a$, $R_b$, $R_c$ and $R_d$, which may be identical or different, represent a hydrogen atom, a $C_1$-$C_4$ alkyl radical or a $C_1$-$C_4$ hydroxyalkyl radical.

The dye composition according to the invention may be in various forms, such as in the form of liquids, creams or gels, or in any other form suitable for dyeing keratin fibres, and in particular human hair.

The process of the present invention is a process, in which the composition according to the present invention as defined above is applied to the fibres.

According to a specific embodiment, the process of the invention is carried out in the presence of an oxidizing agent. This oxidizing agent is applied to the keratin fibres for a period of time sufficient to obtain the desired lightening. The oxidizing agent can be present in the composition comprising the naphthalimide-type compound, it can be added just at the moment of use, or it can be applied simultaneously with or sequentially to the composition containing the naphthalimide-type compound.

According to one variant, the process of the invention comprises the application of the composition of the invention to dark keratin fibres, in particular hair having a tone depth of less than or equal to 6, preferably less than or equal to 4. The term "tone depth" is intended to mean the classification conventionally used in the hair dyeing field, defined in the work by C. Zviak, Science des traitements capillaires [The science of hair treatments], published by Masson, Paris, p. 278 (1988).

Finally, a subject of the invention is a kit for dyeing keratin fibres, comprising a composition comprising, firstly, at least one of the naphthalimide dyes of formulae (I), (II), (III) or (IV), addition salts with an acid and/or solvates mentioned above, and, secondly, an oxidizing agent.

The following examples serve to illustrate the invention without, however, being limiting in nature.

EXAMPLES

Example 1

Synthesis of 3-methyl-1-{3-[(2-methyl-1,3-dioxo-2,3-dihydro-1H-benzo-[de]isoquinolin-6-yl)amino]propyl}-1H-imidazol-3-ium methyl sulphate

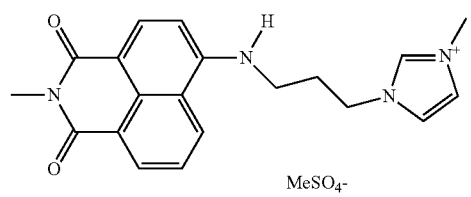

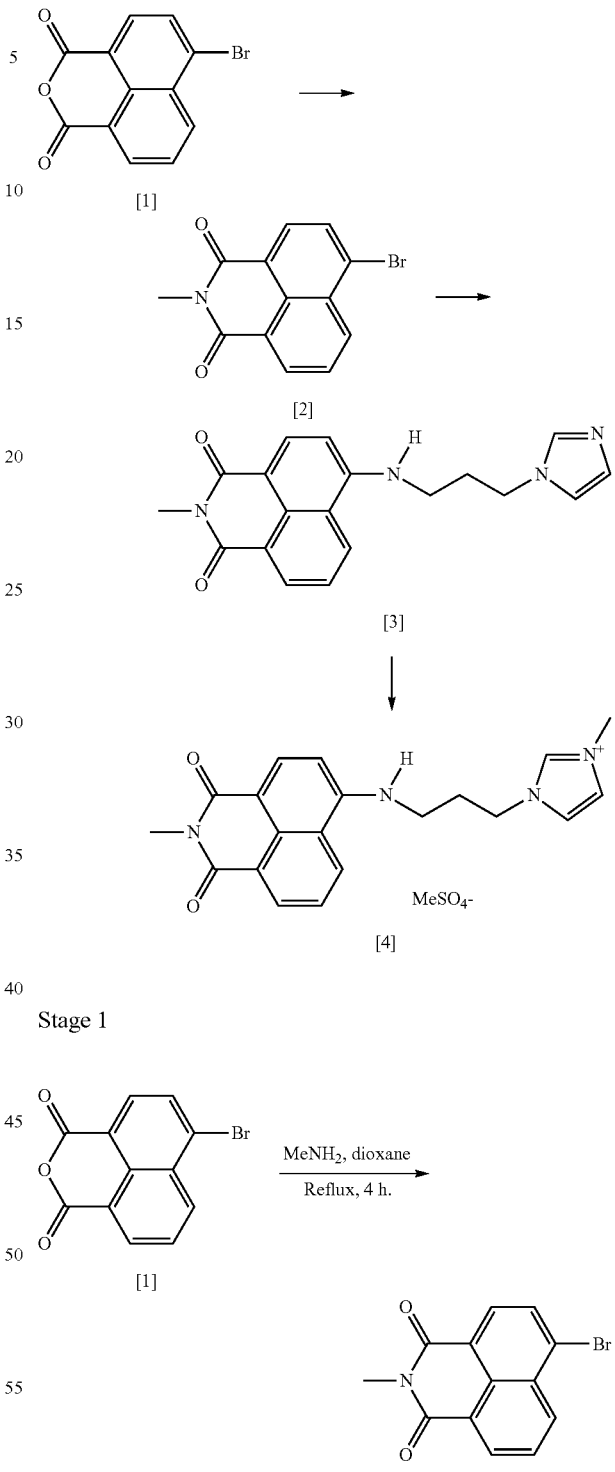

Stage 1

0.76 ml of methylamine is added to a solution of 2.5 g of 4-bromo-1,8-naphthalic anhydride [1] in 45 ml of dioxane. The reaction mixture is refluxed for 4 h. After cooling to ambient temperature, the reaction medium is poured over 50 ml of a water/ice mixture. An orangey/yellow powder precipitates immediately, it is filtered through a Büchner funnel and is then dissolved in a minimum amount of dichloromethane before being dried over magnesium sulphate. After filtration and evaporation, 2.4 g of expected compound [2] are recovered in the form of a yellow powder.

The analyses are in accordance with the expected product.

Stage 2

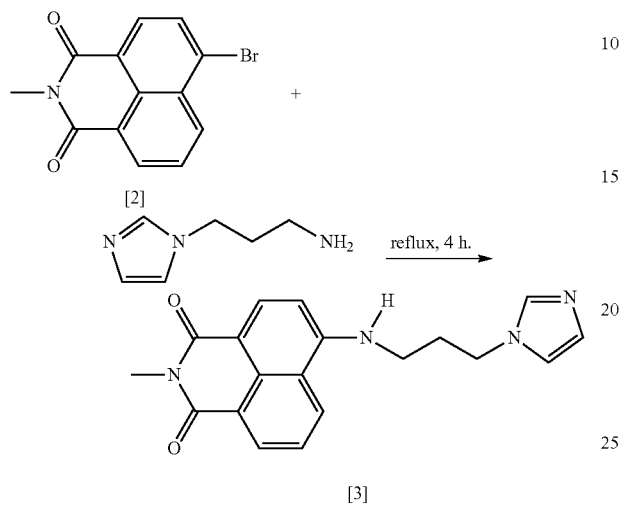

[3]

A solution of 8 g of compound [2] in 20 ml of 1-(3-aminopropyl)imidazole is immersed in a bath preheated to 120° C. The medium is heated for 1 h. The reaction medium is brought back to ambient temperature and then hydrolysed with 70 ml of distilled water. The water becomes coloured and an orange precipitate begins to form. After having left the solution to stand for 12 h at 4° C., the mixture is filtered through a Buchner funnel. The powder obtained is worked with several volumes of dichloromethane and acetone, and then dried over vacuum. 6.2 g of expected compound [3] are recovered in the form of a yellow powder.

The analyses are in accordance with the expected product.

Stage 3

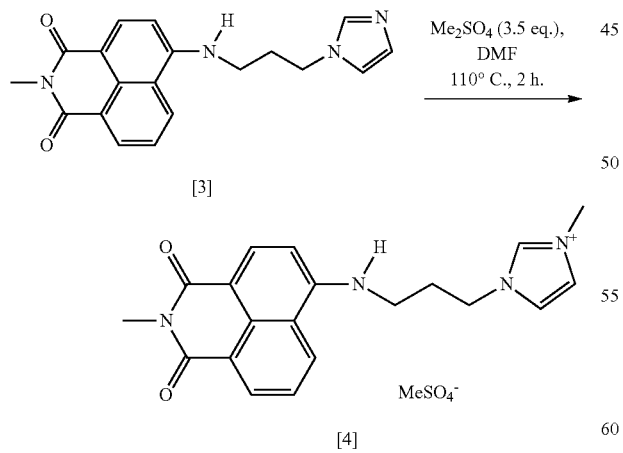

A suspension of 7.3 g of compound [3] in 24 ml of DMF placed under argon is heated in a bath of oil preheated to 110° C., for 5 minutes. After the reaction medium has returned to ambient temperature, 3 ml of dimethyl sulphate are added dropwise. The medium is heated for 2 h at 110° C. The reaction mixture is then submitted to several co-evaporations with toluene in order to remove the DMF. The brown residue obtained is taken up in a minimum amount of methanol, to which ethyl acetate is added until a precipitate is obtained. After filtration under argon, the yellow powder is worked in ethyl acetate (1 h), then ether (1 h) and, finally, chloroform (30 minutes). After filtration and then drying, 9 g of expected compound [4] are recovered in the form of a yellow powder.

The analyses are in accordance with the expected product.

$^1$H NMR (MeOD): 2.3 ppm, m, 2H; 3.8 ppm, s, 3H; 3.6 ppm, s, 3H; 3.4 ppm, s, 3H; 3.5 ppm, t, 2H, 4.4 ppm, t, 2H; 6.8 ppm, d, 1H; 7.3 ppm, s, 1H; 7.5 ppm, d, 1H; d, 1H; 8.3 ppm, d, 1H; 8.5 ppm, d, 2H; 9.0 ppm, s, 1H.

Example 2

Synthesis of 3-methyl-1-{3-[(6-{[3-(3-methyl-1H-imidazol-3-ium-1-yl)propyl]amino}-1,3-dioxo-1H-benzo[de]isoquinolin-2(3H)-yl]propyl}-1H-imidazol-3-ium bis(methyl sulphate)

Compound [7]

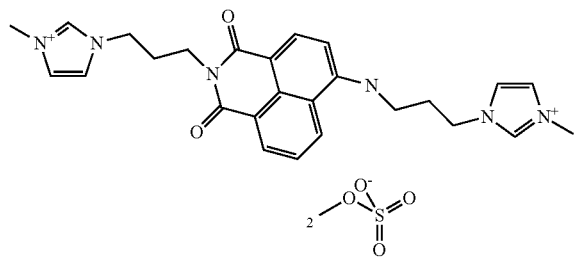

Synthesis Scheme

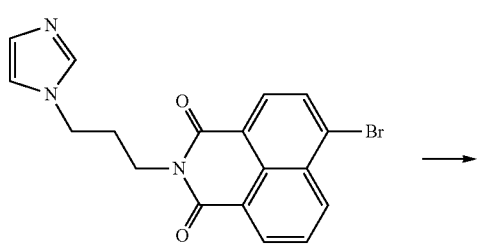

-continued

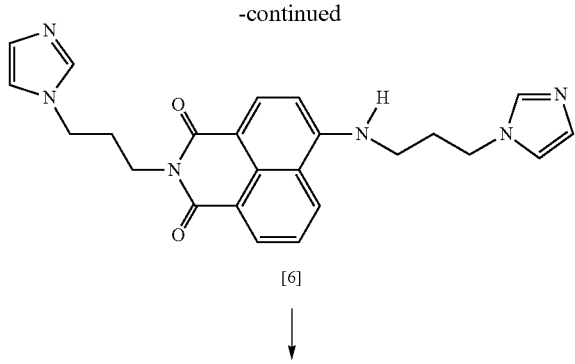
[6]
↓

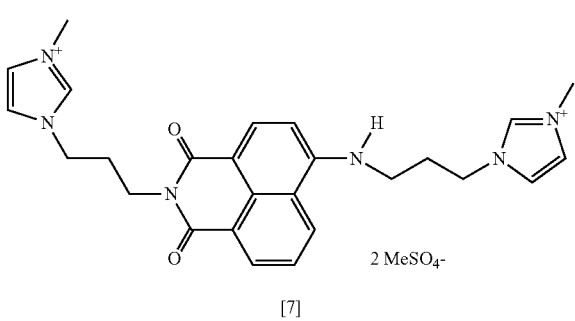
[7]  2 MeSO₄⁻

Stage 1

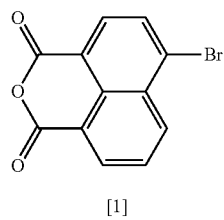
[1]

+

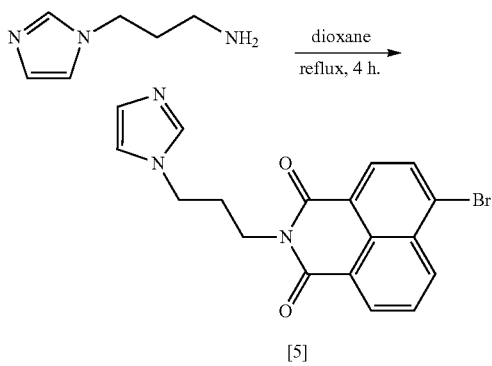
[5]

2.44 ml of 1-(3-aminopropyl)imidazole [2] (20.5 mmol; 1 eq) are added to a brown solution of 5.67 g of 4-bromo-1,8-naphthalic anhydride [1] (20.5 mmol; 1 eq) in 90 ml of dioxane. The reaction mixture is heated at the reflux of dioxane for 4 h.

After cooling of the reaction medium to ambient temperature, the latter is poured into 100 ml of a water/ice mixture. A precipitate forms. The latter is filtered off; and then dissolved in a few millilitres of dichloromethane before being dried over magnesium sulphate. After filtration and evaporation, a yellowish powder is obtained. After purification by silica column chromatography (eluent: 1/1 dichloromethane/acetone), 4.73 g of a yellow-orca powder corresponding to compound [5] are obtained.

The analyses are in accordance with the expected product.

Stage 2

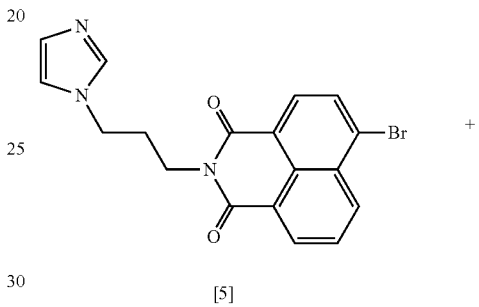
[5]

+

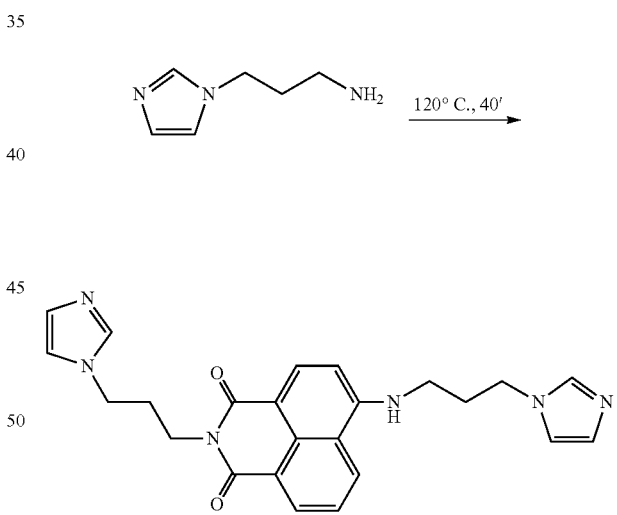
[6]

4.73 g of compound [5] (12.3 mmol; 1 eq) are dissolved by gentle heating in 8.8 ml of 1-(3-aminopropyl)imidazole (73.7 mmol; 6 eq). The reaction mixture is heated at 120° C. for 40 minutes. The blackish residue obtained is brought back to ambient temperature. 60 ml of distilled water are added to this residue and then stirred for 5 minutes. The aqueous phase is extracted with dichloromethane.

The organic phase is subsequently washed with ammonium chloride, dried over sodium sulphate, filtered, and then concentrated under vacuum.

4.83 g of an orange powder corresponding to compound [6] are obtained.

The analyses are in accordance with the expected product.

Stage 3

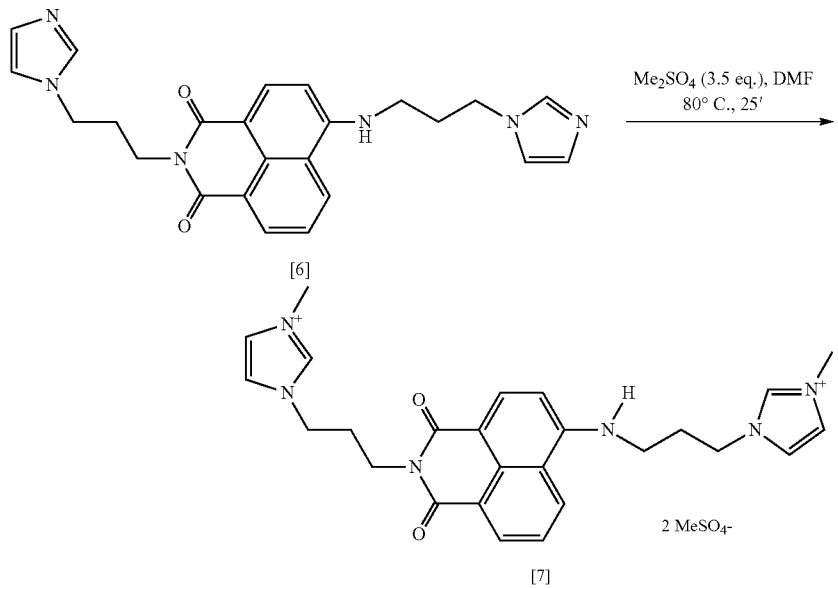

A suspension of 4.83 g of compound [6] (11.2 mmol; 1 eq) in 10 ml are DMF is heated to 80° C. 3.7 ml of dimethyl sulphate (39.4 mmol; 3.5 eq) are then added dropwise to the reaction medium. The reaction mixture is heated at 80° C. for 25 minutes and then brought back to ambient temperature.

Said reaction mixture is then subjected to several co-evaporations with toluene in order to remove the DMF. The brown residue obtained is taken up six times with a mixture consisting of methanol (10 ml), dichloromethane (50 ml) and cyclohexane (50 ml) and vigorously stirred for 5 minutes. The supernatant is systematically removed.

After concentration and then drying under vacuum, 5.20 g of a dark yellow powder corresponding to compound [7] are obtained.

The analyses are in accordance with the expected product.

Examples of Dyes:

| Dye 1 (compound 7) | 3-methyl-1-{3-[(2-methyl-1,3-dioxo-2,3-dihydro-1H-benzo[de]isoquinolin-6-yl)amino]-propyl}-1H-imidazol-3-ium methyl sulphate |
|---|---|
| Dye 2 (compound 4) | 3-methyl-1-{3-[(6-{[3-(3-methyl-1H-imidazol-3-ium-1-yl)propyl]amino}-1,3-dioxo-1H-benzo[de]isoquinolin-2(3H)-yl)propyl}-1H-imidazol-3-ium bis(methyl sulphate) |
| Dye 3 (comparative) | 2-hydroxyethylamino-5-nitroanisole |
| Dye 4 (comparative) | Basic Yellow 87: 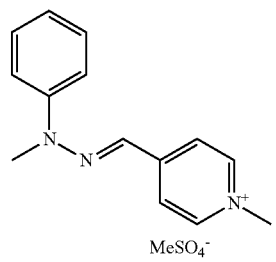 |

Four solutions buffered at pH 9 were prepared by mixing 2 g of ammonium acetate into 40 ml of water. The pH is adjusted by adding aqueous ammonia and the volume is made up to 100 ml by adding deionized water.

Each of the dyes 1 to 4 is dissolved in a buffered solution so as to obtain a dye concentration of $5 \times 10^{-4}$ mol %.

A lock of white hair is brought into contact with the resulting dye solution according to a bath ratio of 10 to 1 (1 g of lock per 10 g of solution).

After a 20 minute wait, the lock is rinsed with deionized water in order to remove the excess dye solution.

With each of the dye solutions, a lock of yellow hair is obtained. Dyes 1 and 2 are visibly more chromatic. When this composition is applied to dark hair (tone depth equal to 4), a lightening optical effect is obtained.

Shampoo Test

Each lock of hair dyed according to the preceding step is hand-washed with a solution comprising 1% by volume of a standard shampoo, for thirty seconds, and then rinsed with 200 ml of water. This process is repeated six times.

It is observed that the intensity of the colour of the locks dyed with the compositions (1 and 2) in accordance with the invention is greater than the intensity of the colour of the locks dyed with the comparative compositions (3 and 4): the dye compositions according to the present application make it possible to obtain colourations that are more resistant to shampooings.

The invention claimed is:

1. A cationic naphthalimide dye corresponding to the compounds of general formula (I) and to the dimers of the compounds (I) corresponding to the following general formulae (II), (III) and (IV):

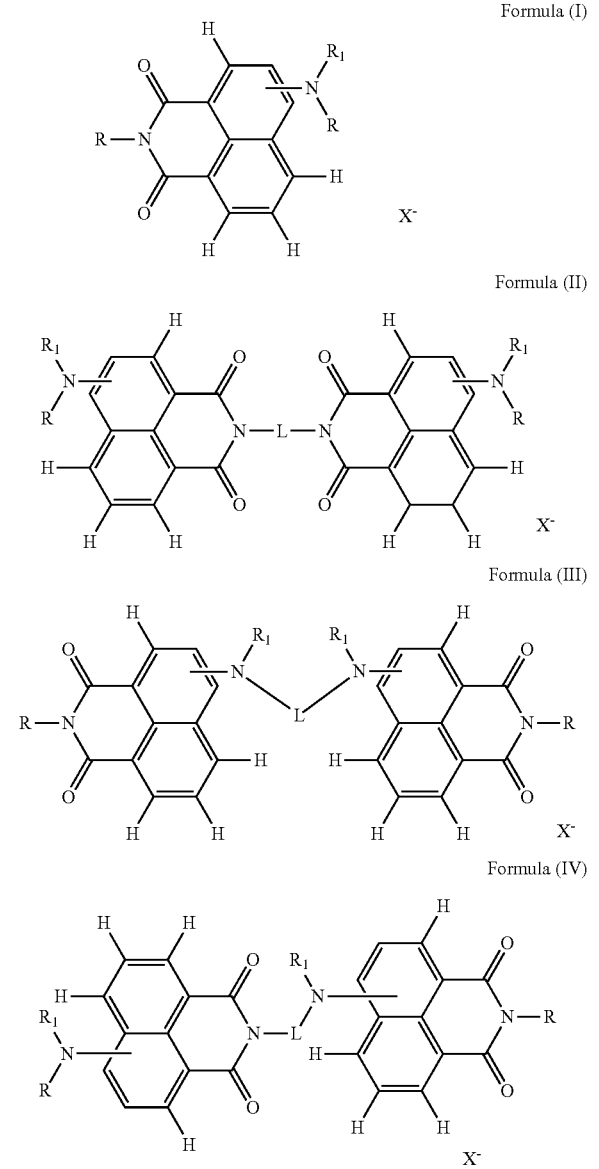

in which formulae (I) to (IV):
the radicals $R_1$, taken separately and independently of one another, represent a hydrogen atom; an optionally substituted $C_1$-$C_4$ alkyl radical, the radicals R, taken separately and independently of one another, represent a hydrogen atom; an aryl or arylalkyl radical, in which the aryl part is optionally substituted; an optionally substituted $C_1$-$C_8$, alkyl radical that is optionally interrupted with one or more heteroatoms chosen from oxygen, nitrogen and sulphur, and that may be substituted with at least one group corresponding to the following formulae (a) and (b):

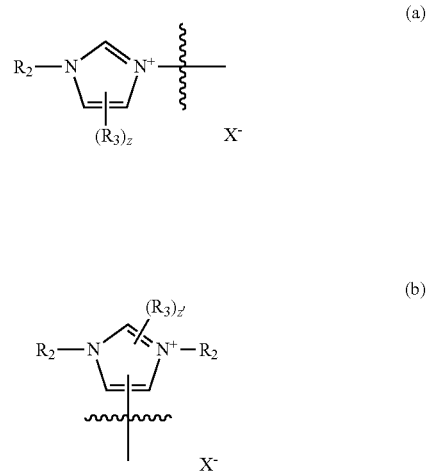

wherein the radical $R_2$ represents an optionally substituted $C_1$-$C_6$ alkyl radical, the radical $R_3$ represents a halogen atom, an optionally substituted $C_1$-$C_6$ alkyl radical, a $C_1$-$C_4$ monohydroxyalkyl radical, a $C_1$-$C_4$ alkoxyl radical, a hydroxycarbonyl radical, a ($C_1$-$C_6$)alkylthio radical, or an amino radical disubstituted with a ($C_1$-$C_4$) alkyl radical, z is an integer between 0 and 3 inclusive, z' is an integer between 0 and 2 inclusive, L is a cationic or non-cationic linker arm;

$X^-$ represents a counterion for ensuring the electroneutrality of the compounds of formulae (I) to (IV);

and to their addition salts with an acid and their solvates.

2. The naphthalimide dye according to claim 1, wherein the radicals $R_1$, which may or may not be identical, independently of one another represent a hydrogen atom, a $C_1$-$C_4$ linear alkyl radical optionally substituted with a hydroxyl, a $C_1$-$C_2$ alkoxyl radical, a ($C_1$-$C_4$)dialkylamino radical, a ($C_1$-$C_3$)alkylcarbonylamino radical, or a ($C_1$-$C_2$)alkyl-sulphonylamino radical.

3. The naphthalimide dye according to claim 2, wherein $R_1$ represents a hydrogen atom or a linear $C_1$-$C_4$ alkyl radical.

4. The naphthalimide dye according to claim 1, wherein L is a non-cationic linker arm chosen from a covalent bond; an optionally substituted $C_2$-$C_{40}$ alkylene radical optionally interrupted with an optionally substituted, optionally condensed, saturated or unsaturated, aromatic or non-aromatic (hetero)cycle comprising from 3 to 7 ring members, wherein the alkylene radical is optionally interrupted with one or more heteroatoms or groups comprising at least one heteroatom, and wherein the linker arm L comprises no azo, nitro, nitroso or peroxo bond; and an optionally substituted phenyl radical.

5. The naphthalimide dye according to claim 4, wherein L is an alkylene linker arm.

6. The naphthalimide dye according to claim 4, wherein L is defined by

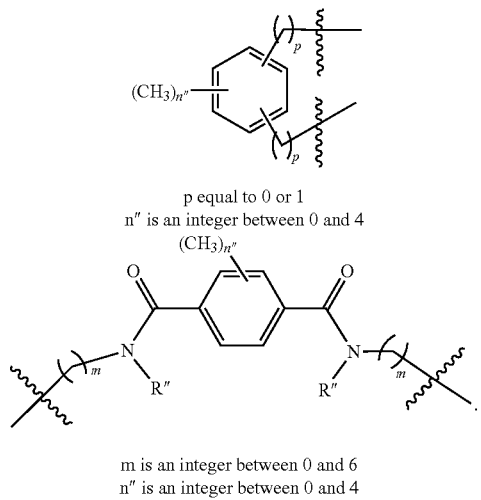

p equal to 0 or 1
n″ is an integer between 0 and 4 m is an integer between 0 and 6
n″ is an integer between 0 and 4

7. The naphthalimide dye according to claim 1 wherein L is a cationic linker arm.

8. The naphthalimide dye according to claim 7, wherein L is a $C_2$-$C_{20}$ alkylene cationic linker arm interrupted with at least one group corresponding to the following formulae;

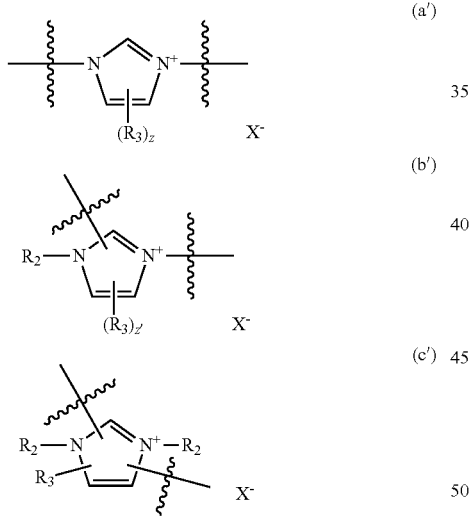

wherein $R_2$, $R_3$, z, z' and X' are as defined in claim 1.

9. The naphthalimide dye according to claim 1, wherein the radicals $R_2$, taken separately and independently of one another, represent a $C_1$-$C_6$ alkyl radical optionally substituted with a hydroxyl, a $C_1$-$C_2$ alkoxyl, a hydroxycarbonyl, a ($C_1$-$C_8$)alkylthio, or an amino radical disubstituted with a $C_1$-$C_4$ alkyl radical.

10. The naphthalimide dye according to claim 1, wherein $R_3$ represents a halogen atom chosen from chlorine and fluorine, a $C_1$-$C_6$ alkyl radical, a $C_1$-$C_4$ monohydroxyalkyl radical, a $C_1$-$C_4$ alkoxyl radical, a hydroxycarbonyl radical, a ($C_1$-$C_6$)alkylthio radical, or an amino radical disubstituted with a $C_1$-$C_4$ alkyl radical.

11. The naphthalimide dye according to claim 1, wherein z and z' are equal to 0.

12. The naphthalimide dye according to claim 1, wherein the radicals R, taken separately and independently of one another, represent a hydrogen atom; a $C_1$-$C_6$, alkyl radical optionally substituted with at least one group corresponding to formula (a) as defined in claim 1; or an aryl or arylalkyl radical wherein the aryl part is optionally substituted.

13. The naphthalimide dye according to claim 12, wherein the radicals R, which may be identical or different, independently of one another, represent a hydrogen atom; a $C_1$-$C_3$ alkyl radical, a hydroxyalkyl radical, an alkoxyalkyl radical, a $C_1$-$C_3$ alkyl radical interrupted with at least one group corresponding to the following formula (a″), a benzyl radical optionally substituted with one or more radicals, which may be identical or different, chosen from the groups hydroxyl, alkoxyl, amino and (di)alkylamino

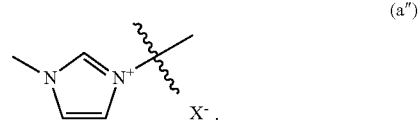

(a″)

14. The naphthalimide dye according to claim 1, wherein X⁻ represents an organic or inorganic counterion chosen from a halide; a hydroxide; a sulphate; a hydrogen sulphate; an alkyl sulphate wherein the linear or branched alkyl part is $C_1$-$C_6$; carbonates and hydrogen carbonates; carboxylic acid salts; alkylsulphonates wherein the linear or branched alkyl part is $C_1$-$C_6$; arylsulphonates wherein the aryl, part is optionally substituted with one or more $C_1$-$C_4$ alkyl radicals; alkylsulphonyls.

15. The naphthalimide dye according to claim 1, chosen from:

The 3-methyl-1-{3-[(2-methyl-1,3-dioxo-2,3-dihydro-1H-benzo[de]isoquinolin-6-yl)amino]propyl}-1H-imidazol-3-ium salt

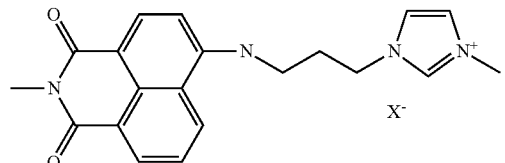

The 1-{3-[6-[(2-hydroxyethyl)amino]-1,3-dioxo-1H-benzo[de]isoquinolin-2(3H)-yl]propyl}-3-methyl-1H-imidazol-3-ium salt

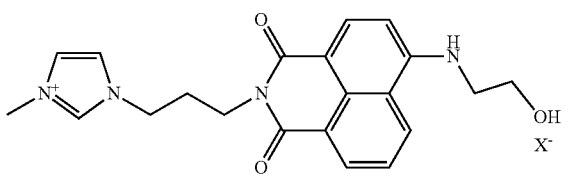

The 3-methyl-1-{3-[(6-{[3-(3-methyl-1H-imidazol-3-ium-1-yl)propyl]amino}-1,3-dioxo-1H-benzo[de]isoquinolin-2(3H)-yl]propyl}-1H-imidazol-3-ium salt:

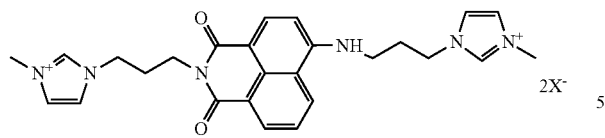 2X⁻

The 3-{5-[(2-ethyl-1,3-dioxo-2,3-dihydro-1H-benzo[de]isoquinolin-6-yl)amino]-pentyl}-1-{3-[(2-ethyl-1,3-dioxo-2,3-dihydro-1H-benzo[de]isoquinolin-6-yl)amino]-propyl}-1H-imidazol-3-ium salt

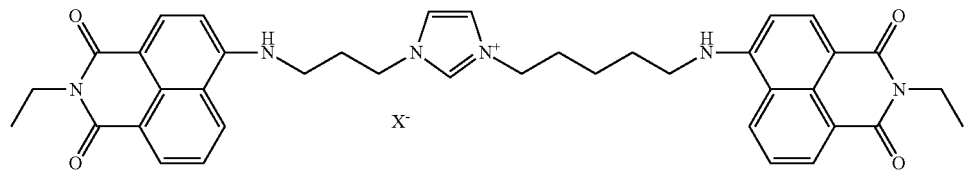

The 3,3'-butane-1,4-diylbis(1-{5-[(2-ethyl-1,3-dioxo-2,3-dihydro-1H-benzo-[de]isoquinolin-6-yl)amino]pentyl}-1H-imidazol-3-ium salt

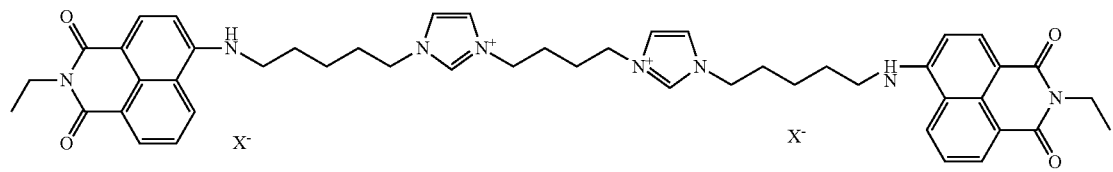

The 3-{5-[(2-ethyl-1,3-dioxo-2,3-dihydro-1H-benzo[de]isoquinolin-6-yl)amino]-pentyl}-1-[3-({2-[3-(1-methyl-1H-imidazol-3-ium-3-yl)propyl]-1,3-dioxo-2,3-dihydro-1H-benzo[de]isoquinolin-6-yl}amino)propyl]-1H-imidazol-3-ium salt

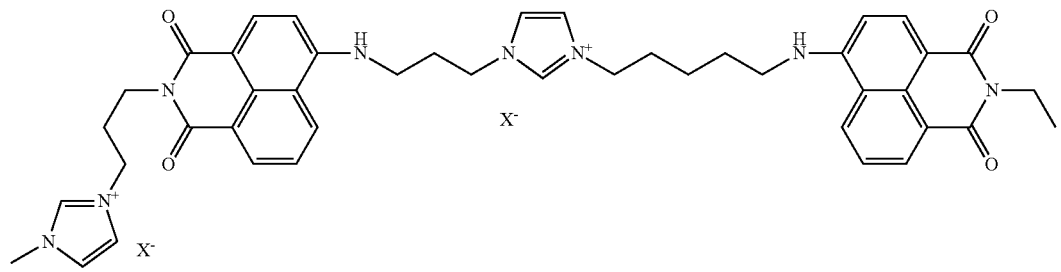

The 1-{5-[(2-ethyl-1,3-dioxo-2,3-dihydro-1H-benzo[de]isoquinolin-6-yl)amino]-pentyl}-3-(4-{1-[5-(-[3-(1-methyl-1H-imidazol-3-ium-3-yl)propyl]-1,3-dioxo-2,3-di-hydro-1H-benzo[de]isoquinolin-6-yl}amino)pentyl]-1H-imidazol-3-ium-3-yl}butyl)-1H-imidazol-3-ium salt

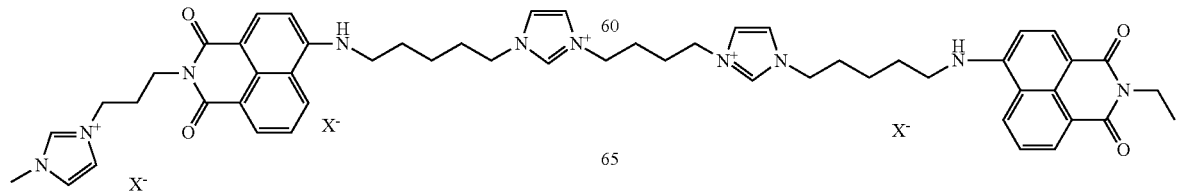

The 1-methyl-3-{3-[6-[(3-{3-[5-({2-[3-(1-methyl-1H-imidazol-3-ium-3-yl-propyl]-1,3-dioxo-2,3-dihydro-1H-benzo[de]isoquinolin-6-yl}amino)pentyl]-1H-imidazol-3-ium-1-yl}propyl)amino]-1,3-dioxo-1H-benzo[de]isoquinolin-2(3H)-yl]propyl}-1H-imidazol-3-ium salt

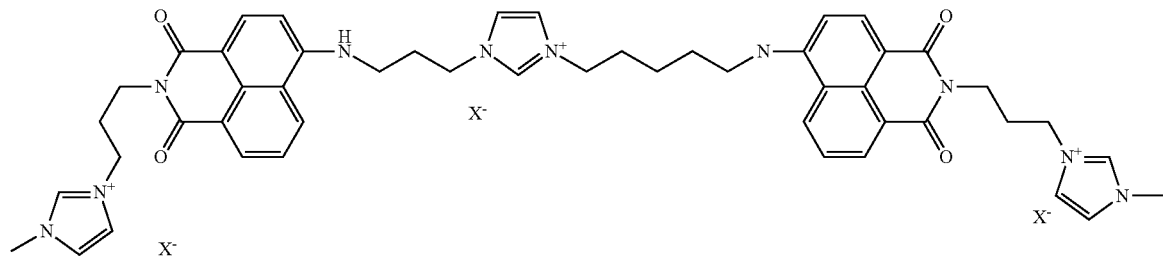

The 3,3'-butane-1,4-diylbis{1-[5-({2-[3-(1-methyl-1H-imidazol-3-ium-3-yl)-propylyl]-1,3-dioxo-2,3-dihydro-1H-benzo[de]isoquinolin-6-yl}amino)pentyl]-1H-imidazol-ium} salt

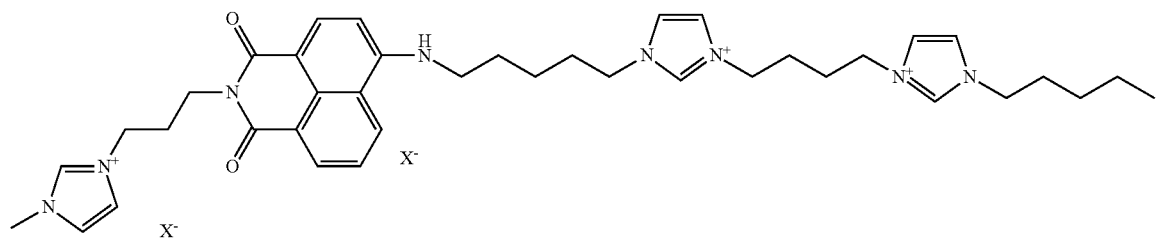

The 1-methyl-3-[3-({2-[3-(3-{5-[6-{[3-(1-methyl-1H-imidazol-3-ium-3-yl)-propyl]amino}-1,3-dioxo-1H-benzo[de]isoquinolin-2(3H)-yl]pentyl}-1H-imidazol-3-ium-1-yl)propyl]-1,3-dioxo-2,3-dihydro-1H-benzo[de]isoquinolin-6-yl} amino)propyl]-1H-imidazol-3-ium salt

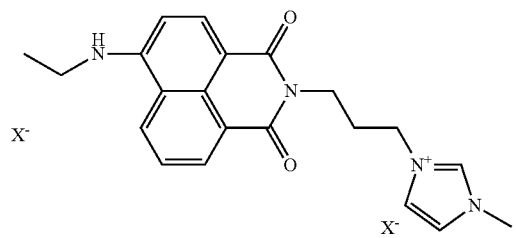

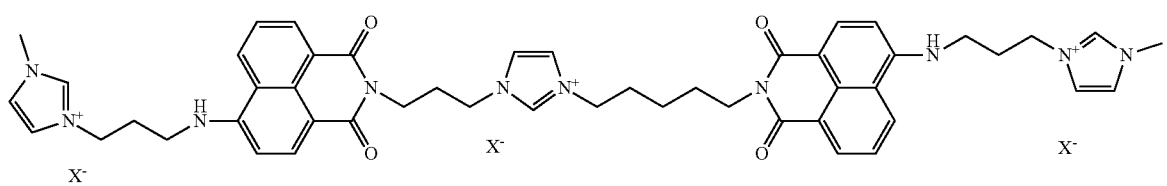

The 3-{6-[6-[bis(2-hydroxyethyl)amino]-1,3-dioxo-1H-benzo[de]isoquinolin-2(3H)-yl]hexyl}-1-{3-[(2-methyl-1,3-dioxo-2,3-dihydro-1H-benzo[de]isoquinolin-6-yl)amino]propyl-1H-imidazol-3-ium salt

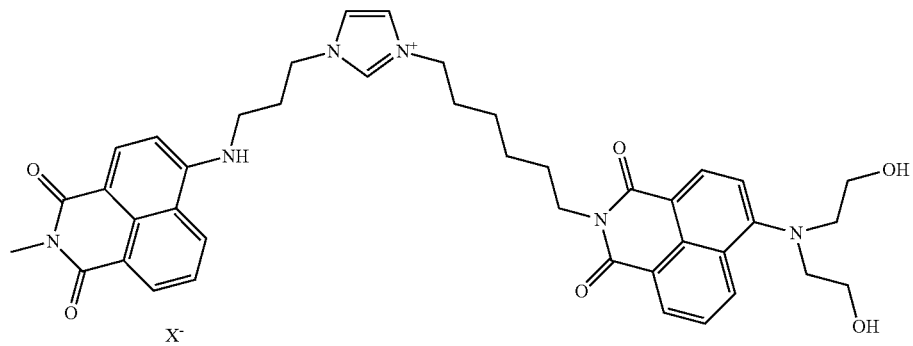

The 3-methyl-1-[3-({2-[6-(1-{3[(2-methyl-1,3-dioxo-2,3-dihydro-1H-benzo-[de]isoquinolin-6-yl)amino]propyl}-1H-imidazol-3-ium-3-yl)hexyl]-1,3-dioxo-2,3-dihydro-1H-benzo[de]isoquinolin-6-yl}amino)propyl]-1H-imidazol-3-ium salt

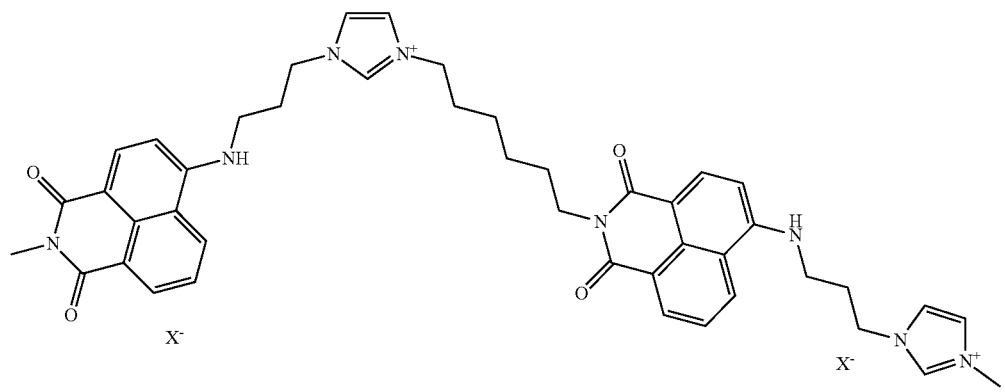

The 1-methyl-3-{3-[6-{[3-(3{6-[6-{[3-(3-methyl-1H-imidazol-3-ium-1-yl)-propyl]amino}-1,3-dioxo-1H-benzo[de]isoquinolin-2(3H)-yl]hexyl}-1H-imidazol-3-ium-1-yl)propyl]amino}-1,3-dioxo-1H-benzo[de]isoquinolin-2(3H)-yl]propyl}-H-imidazol-3-ium salt

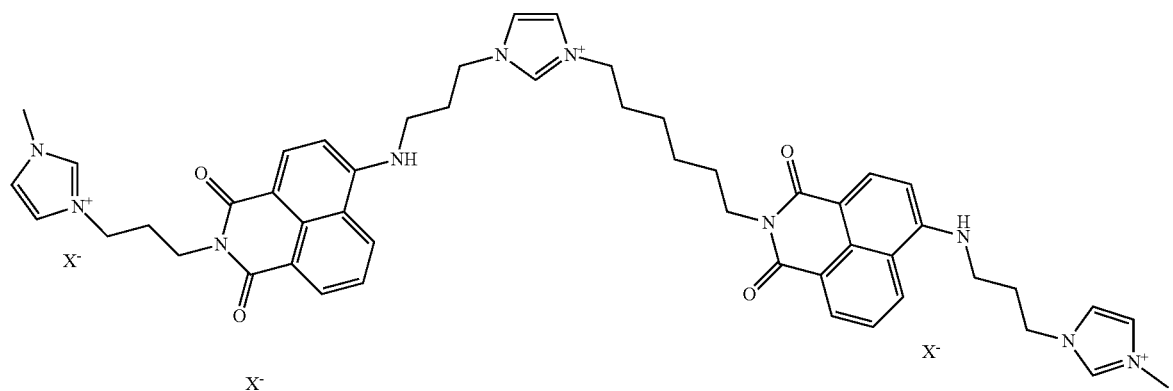

The 3-methyl-1-[3-({2-[6-(1-{6-[6-{[3-(1-methyl-1H-imidazol-3-ium-3-yl)-propyl]amino}-1,3-dioxo-1H-benzo[de]isoquinolin-2(3H)-yl]hexyl}-1H-imidazol-3-ium-3-yl)hexyl]-1,3-dioxo-2,3-dihydro-1H-benzo[de]isoquinolin-6-yl}amino)propyl]-1H-imidazol-3-ium salt

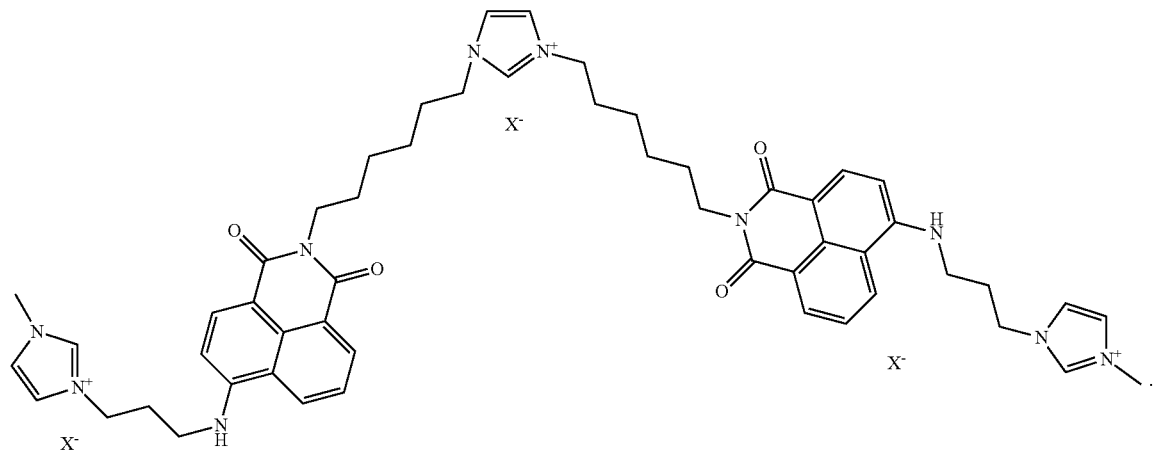

16. The naphthalimide dye according to claim 1, of formula:

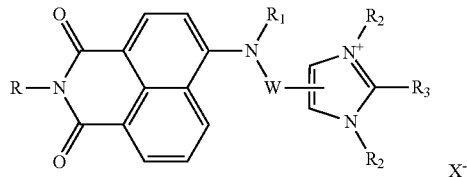

wherein
W represents a $C_1$-$C_8$ alkyl radical,
R, $R_1$, $R_2$, $R_3$ and $X^-$ are as defined as in claim 1.

17. The naphthalimide dye according to claim 1, of formula:

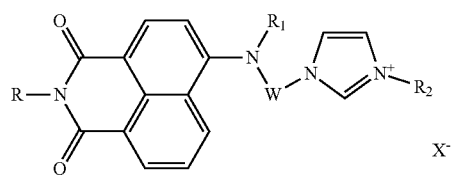

wherein
W represents a $C_1$-$C_8$ alkyl radical,
R, $R_1$, $R_2$ and $X^-$ are as defined as in claim 1.

18. The naphthalimide dye according to claim 1, of formula:

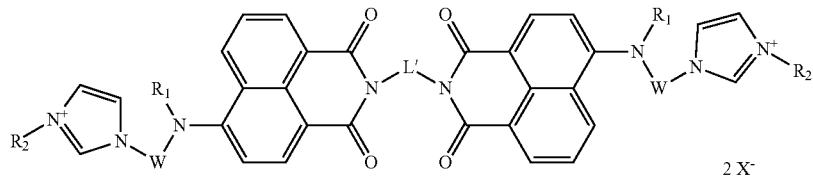

wherein

W represents a $C_1$-$C_8$ radical, $R_1$, $R_2$ and $X^-$ are as defined in claim 1, L' is defined as L in claim 1.

19. The naphthalimide dye according to claim 1, of formula:

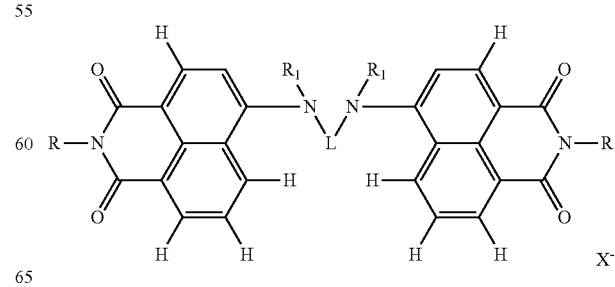

wherein R, $R_1$, L and $X^-$ are as defined in claim 1.

20. The naphthalimide dye according to claim 1, of formula:

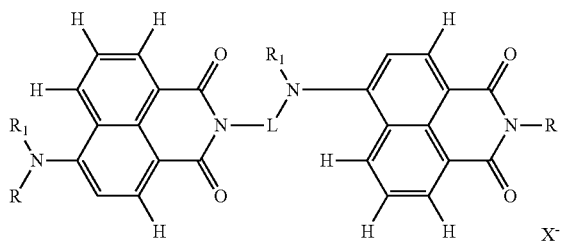

wherein R, $R_1$, L and $X^-$ are as defined in claim 1.

21. A dye composition for dyeing keratin fibers, comprising, in a suitable dye medium, at least one cationic naphthalimide compound according to claim 1.

22. The dye composition according to claim 21, comprising from 0.001% to 10%, by weight of at least one cationic naphthalimide compound, relative to the total weight of the composition.

23. The dye composition according to claim 21, wherein the dye medium comprises at least one organic solvent chosen from $C_1$-$C_4$ lower alcohols; polyols and polyol ethers; aromatic alcohols; and mixtures thereof.

24. The dye composition according to claim 21, also comprising at least one adjuvant chosen from anionic, cationic, non-ionic, amphoteric or zwitterionic surfactants, or mixtures thereof; anionic, cationic, non-ionic, amphoteric or zwitterionic polymers, or mixtures thereof; inorganic or organic thickeners and anionic, cationic, non-ionic and amphoteric polymeric associative thickeners; antioxidants; penetrating agents; sequestering agents; fragrances; buffers; dispersants; conditioners film-forming agents; ceramides; preserving agents and opacifiers.

25. The dye composition according to claim 21, further comprising at least one oxidizing agent chosen from hydrogen peroxide, urea peroxide, alkali metal bromates, persalts, peracids and oxidase enzymes.

26. The dye composition according to claim 25, comprising an oxidizing agent of peroxide type and/or an oxidizing agent of persalt type.

27. The dye composition according to claim 26, comprising, as oxidizing agent, a mixture of hydrogen peroxide and persulphates, hydrogen peroxide alone or persulphate alone.

28. A process for dyeing keratin fibers, comprising application to the fibers of the composition as defined in claim 21.

29. The process according to claim 28, wherein the composition is applied to keratin fibers having a tone depth of less than or equal to 6.

30. The process according to claim 29, wherein the composition according to claim 21 is applied on keratin fibers having a tone depth of less than or equal to 6 in order to lighten said fibers.

31. A process for dyeing keratin fibers comprising application as direct dyes, of at least one of the dye composition as defined in claim 21.

32. A kit for dyeing keratin fibers, comprising, a composition comprising at least one of the naphthalimide dyes of formulae (I), (II), (III) or (IV), addition salts and/or solvates thereof, as defined in claim 1, and, an oxidizing agent.

33. The naphthalimide dye according to claim 4, wherein the alkylene radical comprises $C_2$-$C_{20}$.

34. The naphthalimide dye according to claim 16, wherein W represents a $C_2$-$C_4$ alkyl radical.

35. The naphthalimide dye according to claim 17, wherein W represents a $C_2$-$C_4$ alkyl radical.

* * * * *